US010445880B2

(12) United States Patent
Boppart et al.

(10) Patent No.: US 10,445,880 B2
(45) Date of Patent: Oct. 15, 2019

(54) MOLECULAR IMAGING BIOMARKERS

(71) Applicant: The Board of Trustees of the University of Illinois, Urbana, IL (US)

(72) Inventors: Stephen A. Boppart, Champaign, IL (US); Haohua Tu, Savoy, IL (US); Sixian You, Urbana, IL (US); Yuan Liu, Dublin, CA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 36 days.

(21) Appl. No.: 15/928,818

(22) Filed: Mar. 22, 2018

(65) Prior Publication Data

US 2018/0286044 A1    Oct. 4, 2018

Related U.S. Application Data

(60) Provisional application No. 62/478,355, filed on Mar. 29, 2017.

(51) Int. Cl.
*G01N 21/00*    (2006.01)
*G06T 7/00*    (2017.01)
(Continued)

(52) U.S. Cl.
CPC ....... *G06T 7/0014* (2013.01); *G01N 15/1456* (2013.01); *G01N 21/636* (2013.01); *G01N 21/6486* (2013.01); *G01N 21/65* (2013.01); *G01N 33/483* (2013.01); *G16B 40/00* (2019.02); *G01N 2015/1006* (2013.01); (Continued)

(58) Field of Classification Search
CPC ......... G06T 7/0014; G06T 2207/10064; G06T 2207/30096; G06T 2207/30024; G01N 15/1456; G01N 21/636; G01N 33/483; G01N 21/65; G01N 21/6486; G01N 2015/1006; G01N 2015/144; G01N 2021/653; G01N 2201/06113; G16B 40/00
See application file for complete search history.

(56) References Cited

U.S. PATENT DOCUMENTS

2011/0261349 A1* 10/2011 Cheng ...................... G01J 3/44
356/72

OTHER PUBLICATIONS

Pavillon et al., "Multimodal label-free microscopy," J. Innovative Optical Health Sciences, vol. 7, 1330009 (2014).
(Continued)

*Primary Examiner* — Abdullahi Nur
(74) *Attorney, Agent, or Firm* — Sunstein Kann Murphy & Timbers LLP

(57) ABSTRACT

Methods for label-free characterization of untagged molecules within a biological sample in-situ. The untagged molecules may be constituent of extracellular vesicles, and are excited in the biological sample with at least one wavelength band of light derived from a single stream of optical pulses. Light emitted by the untagged molecules by SHG, THG, 2PAF and 3PAF processes is detected. Separate measures of the biological sample corresponding to light emitted by the untagged molecules in each of the SHG, THG, 2PAF and 3PAF processes are derived. On that basis, normal extracellular vesicles may be differentiated from extracellular vesicles associated with a tumor on the basis of a specified signature of characteristics of images of SHG, THG, 2PAF and 3PAF processes.

16 Claims, 21 Drawing Sheets
(13 of 21 Drawing Sheet(s) Filed in Color)

(51) Int. Cl.
*G01N 33/483* (2006.01)
*G01N 21/65* (2006.01)
*G01N 21/64* (2006.01)
*G16B 40/00* (2019.01)
*G01N 21/63* (2006.01)
*G01N 15/14* (2006.01)
*G01N 15/10* (2006.01)

(52) U.S. Cl.
CPC . *G01N 2015/144* (2013.01); *G01N 2021/653* (2013.01); *G01N 2201/06113* (2013.01); *G06T 2207/10064* (2013.01); *G06T 2207/20081* (2013.01); *G06T 2207/30024* (2013.01); *G06T 2207/30096* (2013.01)

(56) References Cited

OTHER PUBLICATIONS

Lu et al., "Integrated Coherent Anti-Stokes Raman Scattering and Multiphoton Microscopy for Biological Imaging using Spectral Filtering of a Femtosecond Laser," Appl. Phys. Lett., vol. 96, 133701 (2010).
Chu et al., "High-resolution simultaneous three-photon fluorescence and third-harmonic-generation microscopy," Microsc. Res. Tech., vol. 66, pp. 193-197 (2005).
Zomer et al., "In Vivo Imaging Reveals Extracellular Vesicle-Mediated Phenocopying of Metastatic Behavior," Cell, vol. 161, pp. 1046-1057 (2015).
Pope et al., "Simultaneous hyperspectral differential—CARS, TPF and SHG microscopy with a single 5 fs Ti:Sa laser," Opt. Exp., vol. 25, pp. 7096-7106 (2013).
Segawa et al., "Label-free tetra-modal molecular imaging of living cells with CARS, SHG, THG and TSFG (coherent anti-Stokes Raman scattering, second harmonic generation, third harmonic generation and third-order sum frequency generation)," Opt. Exp., vol. 20, pp. 9551-9557 (2012).
Genty et al., "Fiber supercontinuum sources," J. Opt. Soc. Am. B, vol. 24, pp. 1771-1785 (2007).
Boppart, "Label-Free Multimodal Multiphoton Microscopy of Carcinogenesis by Shaping Fiber Supercontinuum Pulses," presented at the Advanced Fluorescence Microscopy Workshop, ISS Fluorescence Foundation (2015).

Li et al., "In vivo and simultaneous multimodal imaging: Integrated multiplex coherent anti-Stokes Raman scattering and two-photon microscopy," Appl. Phys. Lett., vol. 97, 223702 (2010).
Chen et al., "A multimodal platform for nonlinear optical microscopy and microspectroscopy," Opt. Expr., vol. 17, pp. 1282-1290 (2009).
Tu et al., "Coherent Fibers Supercontinuum for Biophotonics," Laser Photon Rev., vol. 7 (2013).
Zipfel et al., "Live tissue intrinsic emission microscopy using multiphoton-excited native fluorescence and second harmonic generation," Proc. Natl. Acad. Sci. USA, vol. 100, pp. 7075-7080 (2003).
Chu et al., "Multimodal nonlinear spectral microscopy based on a femtosecond Cr: forsterite laser," Opt. Lett., vol. 26, pp. 1909-1911 (2001).
Weigelin et al., "Intravital third harmonic generation microscopy of collective melanoma cell invasion: principles of interface guidance and microvesicle dynamics," Intravital, vol. 1, pp. 32-43 (2012).
Weissleder et al., "Shedding light onto live molecular targets," Nat. Med., vol. 9, pp. 123-128 (2003).
Vogler et al., "Multimodal imaging to study the morphochemistry of basal cell carcinoma," J. Biophotonics, vol. 3, pp. 728-736 (2010).
Liu et al., "Multimodal nonlinear mixcroscopy by shaping of a fiber supercontinuum from 900 to 1160 nm," IEEE J. Sel. Top. Quantum Electron., vol. 18, 1209-1214 (2012).
Pegoraro et al., "Optimally chirped multimodal CARS microscopy based on a single Ti:sapphire oscillator," Opt. Expr., vol. 17, pp. 2984-2996 (2009).
Huland et al., "Three-photon excited fluorescence imaging of unstained tissue using a GRIN lens endoscope," Biomed. Opt. Express, vol. 4, pp. 652-658 (2013).
Tu et al., "Stain-Free Histopathology by Programmable Supercontinuum Pulses," Nat. Photonics, vol. 10, pp. 534-540 (2016).
Koenig, "Hybrid multiphoton multimodal tomography of in vivo human skin," IntraVital, vol. 1, pp. 11-26 (2012).
Washburn et al., "Fiber-laser-based frequency comb with a tunable repetition rate," Opt. Expr., vol. 12, pp. 4999-5004 (2004).
Heidt et al., "Mid-infrared ZBLAN fiber supercontinuum source using picosecond diode-pumping at 2 μm," Opt. Expr., vol. 21, pp. 24281-24287 (2013).

* cited by examiner

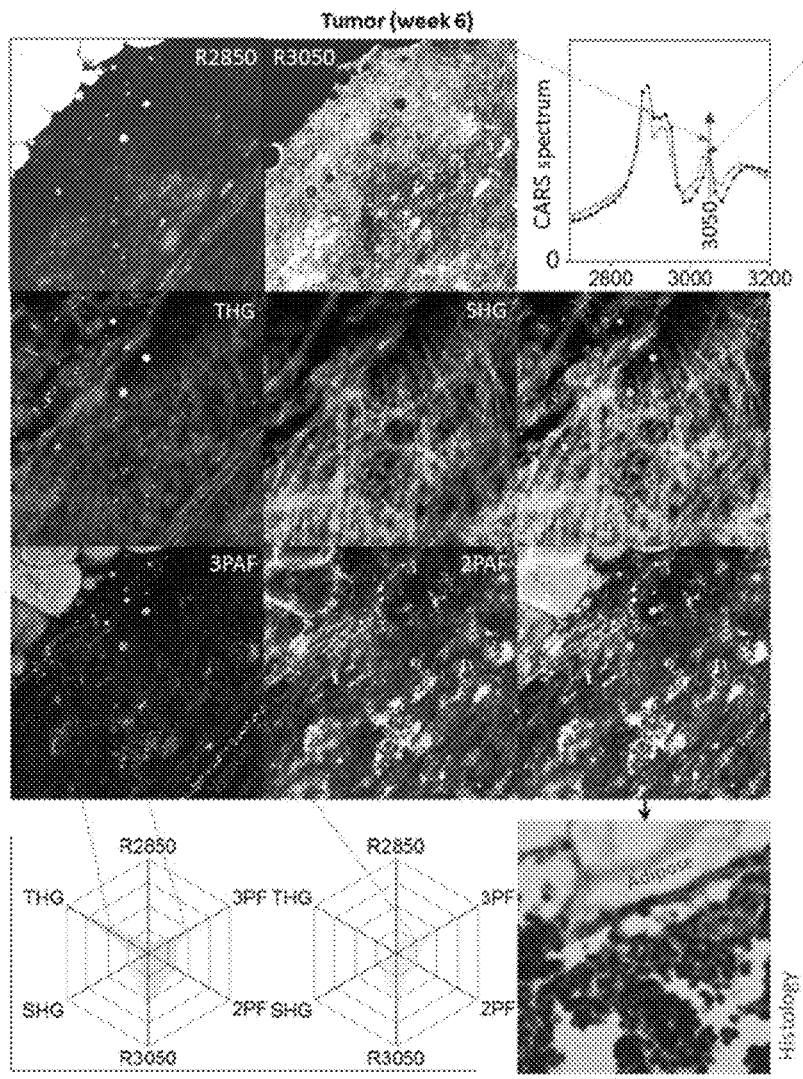
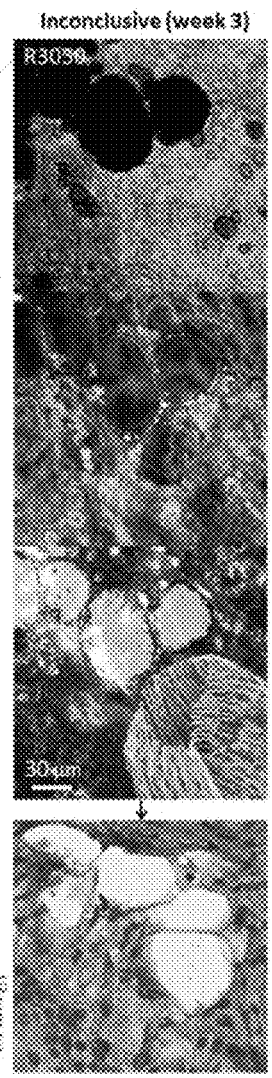
*FIG. 2A*
*FIG. 2C*
*FIG. 2B*

A

| Week_rat/ sampling site | Site related to tumor | Visual | Vesicles, count | R3050 | Class | Tumor microenvironment events* and other biological structures/events (figure reference) |
|---|---|---|---|---|---|---|
| 1_control/a | | - | -, 1 | - | A&S | Lipid breakdown |
| 1_control/b | | - | -, 0 | - | A&S | Lipid breakdown |
| 1_control/c | | - | -, 1 | - | S | Collagen production, lipolysis |
| 1_experiment/a | | - | -, 0 | - | A&S | Lipogenesis lipid breakdown, stromal native cells |
| 1_experiment/b | | +/- | +, >20 | + | S | Hair follicle |
| 1_experiment/c | | +/- | +, 9 | + | S | Mammary duct, lipolysis |
| 1_experiment/d | | - | -, 0 | - | A&S | Nerve, stromal native cells |
| 2_control/a | | - | -, 0 | - | A | Fluorescent protein mass |
| 2_control/b | | - | -, 0 | - | S | Native cells, lipolysis |
| 2_control/c | | - | -, 0 | - | A | Regular adipocytes |
| 2_experiment/a | | - | -, 1 | - | S | Native cells, mammary duct |
| 2_experiment/b | | - | -, 2 | - | S | Mammary duct, lipolysis native cells (Fig. 2, inset 2) |
| 2_experiment/c | | - | -, 5 | - | S | Stromal native cells |
| 2_experiment/d | | - | -, 4 | - | A&S | Nerve |
| 2_experiment/e | | - | -, 0 | - | A&S | Nerve |
| 3_control/a | | - | -, 2 | - | A | Lipolysis |
| 3_control/b | | - | -, 0 | - | A | Regular adipocytes |
| 3_control/c | | - | -, 4 | - | S | Collagen production, native cells, nerve |
| 3_experiment/a | | + | +, >20 | + | A&S | Lymphangiogenesis, stromal native cells, fluorescent protein mass |
| 3_experiment/b | | + | +, >20 | + | T&S | Collagen cross-linking, tumor (cells) |
| 3_experiment/c | | - | -, 1 | - | A | Regular adipocytes |
| 3_experiment/d | | - | -, 0 | - | A&S | Stromal native cells |
| 3_experiment/e | | - | -, 4 | - | A&S | Collagen ring |
| 4_control/a | | - | -, 0 | - | A | Regular adipocytes, native cells among adipocytes, crystallization |
| 4_control/b | | - | -, 0 | - | A&S | Lipid breakdown, native cells |
| 4_experiment/a | On site | + | +, >20 | + | A&S | Lipid breakdown |
| 4_experiment/b | On site | + | -, 10 | + | A&S | Fibrosis, stromal native cells | continued on next page

| Week_rat/ sampling site | Site related to tumor | Visual | Vesicles, count | R3050 | Class | Tumor microenvironment events* and other biological structures/events (figure reference) |
|---|---|---|---|---|---|---|
| 4_experiment/c | On site | + | +, >20 | + | T | Collagen cross-linking, tumor (cells) |
| 4_experiment/d | 2-5 mm | +/- | +, 13 | + | A&S | Lipid breakdown, crystallization |
| 5_control/a | | - | -, 0 | - | S | Lipolysis |
| 5_control/b | | - | -, 3 | - | A&S | Lipolysis |
| 5_control/c | | - | -, 6 | - | S | Stromal lipid dispersion, lipolysis |
| 5_experiment/a | On site | + | +, 8 | + | T/S | Basement membrane degradation, reorganized collagen, tumor (cells) |
| 5_experiment/b | On site | + | +, 18 | + | A&S | Non-native cell recruitment, collagen production, stromal native cells (Fig. 3E) |
| 5_experiment/c | On site | + | +, 17 | + | T | Basement membrane degradation, non-native cell recruitment, reorganized collagen, tumor (cells) (Fig.3C) |
| 5_experiment/d | On site | + | +, >20 | + | S&T | Angiogenesis, blood cells, tumor (cells) |
| 5_experiment/e | On site | + | +, 9 | + | A&S | Lipid breakdown |
| 5_experiment/f | 10 mm | - | -, 0 | - | A&S | Lymphatic vessel, stromal native cells |
| 5_experiment/g | 10 mm | - | -, 0 | - | A | Regular adipocytes |
| 6_control/a | | - | -, 1 | - | A&S | Vessel, stromal native cells |
| 6_control/b | | - | -, 0 | - | S | Lipolysis, stromal lipid dispersion (Fig. 2, inset 1) |
| 6_control/c | | - | -, 0 | - | A&S | Native cells among adipocytes, crystallization |
| 6_experiment/a | On site | + | +, 8 | + | A&S | Angiogenesis, lipolysis, stromal native cells |
| 6_experiment/b | On site | + | +, >20 | + | A&S | Angiogenesis, stromal native cells |
| 6_experiment/c | 2-5 mm | +/- | +, 7 | + | S | Mammary ducts |
| 6_experiment/d | 10 mm | - | -, 0 | - | A&S | Stromal native cells, collagen production |

*continued on next page*

| Week_rat/ sampling site | Site related to tumor | Visual | Vesicles, count | R3050 | Class | Tumor microenvironment events* and other biological structures/events (figure reference) |
|---|---|---|---|---|---|---|
| 7_control/a | | +/- | +, 13 | + | S | Lymphangiogenesis, non-native cell recruitment (Fig. 3B) |
| 7_control/b | | +/- | -, 5 | - | A&S | Angiogenesis, non-native cell recruitment, lipolysis, stromal native cells (Fig. 3A) |
| 7_control/c | | - | -, 0 | - | A | Regular adipocytes |
| 7_experiment/a | On site | + | +, >20 | + | A&S | Non-native cell recruitment, reorganized collagen, nerve |
| 7_experiment/b | On site | + | +, >20 | + | A&S | Angiogenesis, lymphangiogenesis, reorganized collagen, fibroblast activation, nerve |
| 7_experiment/c | 2-5 mm | +/- | +, 12 | + | A&S | Lipolysis, stromal lipid dispersion |
| 7_experiment/e | 10 mm | - | -, 5 | - | S | Stromal lipid dispersion |
| 8_control/a | | - | -, 2 | - | A | Native cells among adipocytes |
| 8_control/b | | - | -, 0 | - | A | Regular adipocytes |
| 8_experiment/a | On site | + | +, 18 | + | T/S | Reorganized collagen, tumor (cells) (Fig. 3D) |
| 8_experiment/b | 2-5 mm | +/- | +, 16 | + | A&S | Mammary duct, stromal native cells, lipolysis (Fig. 4, inset 2) |
| 8_experiment/e | 2-5 mm | +/- | +, 16 | + | A&S | Lipolysis (Fig. 4, inset 1) |
| 9_control/a | | - | -, 1 | - | A | Native cells among adipocytes |
| 9_experiment/a | On site | + | -, 1 | - | T | Tumor necrosis |
| 9_experiment/b | On site | + | -, 0 | - | T | Tumor necrosis |
| 9_experiment/d | 2-5 mm | +/- | +, 15 | + | A&S | Lipolysis, native cells deformed adipocytes |
| 9_experiment/f | 10 mm | - | -, 2 | - | A&S | Stromal native cells, lipolysis |

| Week_rat/ sampling site | Site related to tumor | Visual | Vesicles/ R3050 | Class | Tumor microenvironment events* and other biological structures/events (figure reference) |
| --- | --- | --- | --- | --- | --- |
| 7_control/d | 10 min | - | - | A&S | Stromal native cells, lipolysis |
| 7_experiment/d | On site | + | + | A&S | Lymphangiogenesis, angiogenesis non-active cell recruitment, reorganized collagen, fibroblast activation, fibrosis, nerve, blood cells, tumor (cells) (Fig. 1) |
| 8_control/b | - | - | - | A&S | Native cells (Fig., main) |
| 8_control/d | - | - | - | A | Regular adipocytes |
| 8_experiment/c | On site | + | + | T&S | Reorganized collagen, basement membrane degradation, lymphangiogenesis, non-native cell recruitment, abgiogenesis, tumor (cells), native cells |
| 8_experiment/d | On site | + | + | A&S | Fibroblast activation, fibrosis, angiogenesis, reorganized collagen, non-native cell recruitment, native cells, lipolysis, tumor cells |
| 9_control/b | - | - | - | A | Native cells |
| 9_experiment/c | On site | + | - | T | Tumor necrosis |
| 9_experiment/e | 2-5 mm | +/- | + | A&S | Lipolysis, native cells, deformed adipocytes (Fig. 4, main) |

*Tumor microenvirement events are in bold font.

*FIG. 12*

MOLECULAR IMAGING BIOMARKERS

The present application claims priority from U.S. Provisional Patent Application Ser. No. 62/478,355, filed Mar. 29, 2017, and incorporated herein by reference.

This invention was made with government support under grant CA166309 awarded by the National Institutes of Health. The government has certain rights in the invention.

TECHNICAL FIELD

The present invention relates to apparatus and methods for in-situ label-free imaging of molecules, and, more particularly, molecules associated with extracellular vesicles using concurrent multimodal nonlinear imaging.

BACKGROUND ART

Over the course of recent years, stain-free histopathology of fresh tissue within minutes has been established by diverse nonlinear optical processes to improve upon conventional histotechnology based on single-photon microscopy. The stain-free non-linear imaging techniques obviate time-consuming paradigmatic elements of standard histology procedures. A summary of various of the nonlinear optical modalities employed is provided by Pavillon et al., "Multimodal label-free microscopy," J. Innovative Optical Health Sciences, vol. 7, 1330009 (2014), incorporated herein by reference.

Phospholipid-enclosed extracellular vesicles have been the subject of study since the 1980s, however the in vivo role of extracellular vesicles has been elusive because, prior to the present invention, there has been no method for observing them label-free in live tissue.

Techniques are known in the art for imaging media, including biological media, using each of the constituent nonlinear modalities of the current invention, namely second harmonic generation (SHG), third harmonic generation (THG), two-photon auto-fluorescence (2PAF), three-photon auto-fluorescence (3PAF), and coherent anti-Stokes Raman scattering (CARS). Auto-fluorescence arises due to photoexcitation of various molecules naturally occurring in biological matter, with flavins (e.g., flavin adenine dinucleotide (FAD)) and nicotinamide adenine dinucleotide (NADH) notably used as biomarkers in live cells. Integration of coherent anti-Stokes Raman imaging with multiphoton imaging has also been discussed, as by Lu et al., "Integrated Coherent Anti-Stokes Raman Scattering and Multiphoton Microscopy for Biological Imaging using Spectral Filtering of a Femtosecond Laser," Appl. Phys. Lett., vol. 96, 133701 (2010), which is incorporated herein by reference.

The use of multimodal imaging and CARS in an in-vivo and simultaneous context has been shown by Li et al., "In vivo and simultaneous multimodal imaging: Integrated multiplex coherent anti-Stokes Raman scattering and two photon microscopy," Appl. Phys. Lett, vol. 97, 223702 (2010), which is incorporated by reference. Another multimodal platform is described by Chen et al., "A multimodal platform for nonlinear optical microscopy and microspectroscopy," Opt. Expr., vol. 17, pp. 1282-90 (2009), incorporated herein by reference.

Prior to the present invention, described in detail below, it was believed in the art that imaging in the modalities of THG and autofluorescence were mutually incompatible for simultaneous imaging of biological materials in situ. That is because UV absorption of the third harmonic placed a lower bound on the THG excitation wavelength, while, at an infrared wavelength compatible with THG, the autofluorescence signal for either 2PAF or 3PAF was too weak to achieve a meaningful signal to noise, unless excitation intensities were increased to the point where average incident power leads to biological photodamage. For the foregoing reasons, to the best of the knowledge of the inventors, in-situ imaging of extracellular vesicles has eluded all known techniques, and, in order to unlock the potential of four- or five-mode imaging of the sort taught herein, an invention was required.

One dimension of some embodiments the invention described below concerns a supercontinuum source. Several integrated fiber sources, such as a supercontinuum source using photonic crystal fiber (PCF) pumped with 100-200 fs pulses from $Yb^{3+}$ fiber lasers, are discussed by Genty et al., "Fiber supercontinuum sources," J. Opt. Soc. Am. B, vol. 24, pp. 1771-85 (2007), incorporated herein by reference. The use of supercontinuum sources in a context of biophotonics is surveyed by Tu et al., "Coherent Fibers Supercontinuum for Biophotonics," Laser Photon Rev., vol. 7 (2013), which is incorporated herein by reference.

Over the last decade, two platforms of label-free epi-detected imaging have stood out as viable clinical platforms for multiphoton microscopy: One, demonstrated by Zipfel et al., "Live tissue intrinsic emission microscopy using multiphoton-excited native fluorescence and second harmonic generation," Proc. Natl. Acad. Sci. USA, vol. 100, pp. 7075-80 (2003), which is incorporated here by reference, simultaneously collects the structural information (noncentrosymmetry) of second-harmonic generation (SHG) and the functional information of two-photon auto-fluorescence (2PAF) excited at a short-wavelength (SW) band of ≤950 nm, and is thus termed "SW-SHG&2PAF imaging." The other, described by Chu et al., "Multimodal nonlinear spectral microscopy based on a femtosecond Cr: forsterite laser," Opt. Lett., vol. 26, pp. 1909-11 (2001) (hereinafter, Chu, 2001), incorporated herein by reference, simultaneously collects the structural information of SHG and other structural information (optical heterogeneity) of third-harmonic generation (THG) excited at a long-wavelength (LW) band of 1000 nm, and is thus termed "LW-SHG&THG imaging."

The former platform has been critically limited by highly nonlinear photodamage, and, to a lesser degree, insufficient structural information when tissue lacks noncentrosymmetry (SHG contrast), while the later platform has been critically limited by the absence of functional information including auto-fluorescence intensity and lifetime. The two platforms complement each other, but have long resisted a synergistic integration to simultaneously collect SHG, THG, and auto-fluorescence signals by one single (single-beam fixed-wavelength) excitation. Their simple combination using sequential SW and LW excitations coupled with sequential signal detections on the same field-of-view, as practiced, for example, in Weigelin et al., "Intravital third harmonic generation microscopy of collective melanoma cell invasion: principles of interface guidance and microvesicle dynamics," Intravital, vol. 1, pp. 32-43 (2012), incorporated herein by reference, not only increases photodamage risk and prevents rigorous spatial co-registration between sequentially detected signals, but also complicates the corresponding fiber-based endoscope or handheld probe afforded by both platforms. Because THG contrast cannot be generated from the SW-SHG&2PAF platform due to UV absorption by tissue and standard optics, there has long been a profound need to introduce functional information to the LW-SHG&THG platform in order to empower multiphoton microscopy as real-time stain-free histology.

Various treatments of the tumor microenvironment in the prior literature have included a non-reductionist view of cancer, interactions at the tumor-host interface, a wound-healing analogue of tumor development, the concept of "seed and soil", the bipolar effects of stroma in the tumor "organ", and the Darwinian (environmental) selection of metastatic tumor cells. Signature events occurring in the tumor microenvironment include: (I) recruitment or infiltration of non-native cells such as immune inflammatory cells and bone-marrow-derived cells, and activation or alteration of fibroblasts (or other native cells for promotion of tumor malignancy and protection from immune attack; (II) a mechanically reorganized extracellular matrix, including degraded basement membrane and rearranged, cross-linked, or fibrotic collagen for enhanced local invasion; (III) angiogenesis and lymphangiogenesis for primary tumor growth and subsequent metastasis; (IV) modulation of stroma by small (<1 µm) tumor-associated extracellular vesicles for pre-conditioning proliferation, invasion, and metastasis of tumor cells; and (V) metabolic switch from energy production to biomass production (biosynthesis), i.e., a reinterpreted Warburg effect that enriches amino acids, nucleotides, and fatty acids, discussed by Vander Heiden et al., "*Understanding the Warburg effect: the metabolic requirements of cell proliferation,*" Science, vol. 324, pp. 1029-33 (2009), which is incorporated herein by reference.

The metabolic switch has long been masked in oxygen- and nutrient-rich tissue cultures, and has therefore been treated as an adaption to the stressful tumor microenvironment. Each of these tumor microenvironment events has been investigated with exogenous molecular labeling probes to identify biomolecules of interest (rare signaling molecules or bulk substances) within biological samples (cell/tissue cultures, xenografts, dissected specimens, transgenic animals, cancer animal models, living subjects, etc.) under in vitro, ex vivo, intravital, or in vivo conditions. However, the interrelation between the events at the macroscopic scale (I-III) and microscopic scale (IV, V) remains elusive due to the lack of an imaging methodology to observe them in concert, in spatially-resolved ways, and without perturbative labels.

Optical imaging can be a promising approach, suggested, among others, by Weissleder et al., "*Shedding light onto live molecular targets,*" Nat. Med., vol. 9, pp. 123-28 (2003), incorporated herein by reference, to study this interrelation, as long as the molecular labeling agents, including genetic reporters that may affect the living system through genetic manipulation, are avoided to eliminate unexpected perturbations to the tumor microenvironment.

Also, to retain more authentic physiology during carcinogenesis, imaging should be performed in non-xenograft tissues, and using a reflection mode (epi-) geometry so that these events in the future can be potentially monitored in clinical scenarios to evaluate therapeutic strategies. Along this path, linear microscopy techniques using photoacoustics or optical frequency domain imaging, targeting single-photon absorption or scattering contrast, has visualized angiogenesis and lymphangiogenesis. However, the molecular specificity, which is crucial in the era of molecular oncology, has not been satisfactory using the linear microscopy techniques.

Alternatively, nonlinear microscopy targeting two-photon optical noncentrosymmetry contrast $\chi^{(2)}_{SHG}$ and three-photon excited auto-fluorescence contrast $AF^{(3)}$ has imaged reorganized collagen and intrinsic fluorophores, respectively. Similarly, nonlinear microscopy has further visualized tumor cells through two-photon excited auto-fluorescence contrast $AF^{(2)}$ and blood cells/vessels through the molecular vibration contrast of coherent anti-Stokes Raman scattering $\chi^{(3)}_{CARS}$. Thus, previously used cell-tracking fluorescent proteins and injected angiogenesis-revealing agents may be avoided. Also, the $\chi^{(3)}_{CARS}$ contrast and three-photon optical heterogeneity contrast $\chi^{(3)}_{THG}$ have revealed the metabolic alteration to lipid/protein ratio and the release of extracellular vesicles in tissue, respectively. These scattered efforts call for a multicontrast (multimodal) nonlinear imaging platform that, unlike multimodal platforms of the prior art, is capable of collecting spatially co-registered images with different contrasts that include THG and 3PAF of unlabelled biological moieties.

SUMMARY OF EMBODIMENTS OF THE INVENTION

In accordance with one embodiment of the present invention, a method is provided for characterizing an untagged molecule within a biological sample in-situ. The method has steps of:

exciting the untagged molecule in the biological sample with at least one wavelength band of light derived from a single stream of optical pulses;

concurrently detecting light emitted by the untagged molecules of the biological sample by SHG, THG, 2PAF and 3PAF processes; and deriving separate measures of the biological sample corresponding to light emitted by the untagged molecules in each of the SHG, THG, 2PAF and 3PAF processes.

In accordance with other embodiments of the invention, methods are provided for characterizing extracellular vesicles within a biological sample in-situ. The method has steps of:

exciting untagged molecules constituent of the extracellular vesicles in the biological sample with at least one wavelength band of light derived from a single stream of optical pulses;

concurrently detecting light emitted by the untagged molecules of the biological sample by SHG, THG, 2PAF and 3PAF processes; and deriving separate measures of the biological sample corresponding to light emitted by the untagged molecules in each of the SHG, THG, 2PAF and 3PAF processes.

In accordance with other embodiments of the present invention, the method has a further step of imaging at least a portion of the biological sample in at least one of the modalities of SHG, THG, 2PAF and 3PAF.

In certain other embodiments of the invention, the single stream of optical pulses is derived from a coherent supercontinuum distribution of light energy.

In accordance with further embodiments of the present invention, there may be an additional step of detecting light derived from the single stream of optical pulses by coherent anti-Stokes Raman scattering by the untagged molecules, optionally including excitation of the coherent anti-Stokes Raman scattering by a frequency-chirped pulse.

In accordance with yet further embodiments of the present invention, the SHG, THG, 2PAF and 3PAF processes may be excited by a single excitation pulse.

In accordance with other embodiments, there may be an additional step of differentiating normal extracellular vesicles from extracellular vesicles associated with a tumor on the basis of a specified signature of characteristics of images of SHG, THG, 2PAF and 3PAF processes. Differentiation of the normal extracellular vesicles from extracellular vesicles associated with a tumor may be based at least on a specified signature of characteristics of images of SHG, THG, 2PAF and 3PAF and employs machine learning. The tumor may be characterized with respect to a grade associated with aggressiveness of the tumor on the basis of the specified signature of characteristics of images of SHG, THG, 2PAF and 3PAF processes, and that characterization may employ machine learning.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of the invention will be more readily understood by reference to the following detailed description, taken with reference to the accompanying drawings, in which:

FIGS. 2A-2C show mesoscopic organization of biological microstructures revealed in co-localized multiphoton images of two rat mammary specimens, in accordance with methods of the present invention.

FIGS. 11A-11C present Table 3, listing results of a longitudinal animal test of extracellular vesicles and $\chi^{(3)}_{R3050}$ as quantitative breast cancer indicators within a constant field-of-view (0.19×0.19 mm$^2$).

FIG. 12 presents Table 4, listing results of a longitudinal animal test of extracellular vesicles and $\chi^{(3)}_{R3050}$ as quantitative breast cancer indicators within a constant field-of-view (0.57×0.57 mm$^2$).

DETAILED DESCRIPTION OF EMBODIMENTS OF THE INVENTION

Figure 1A:
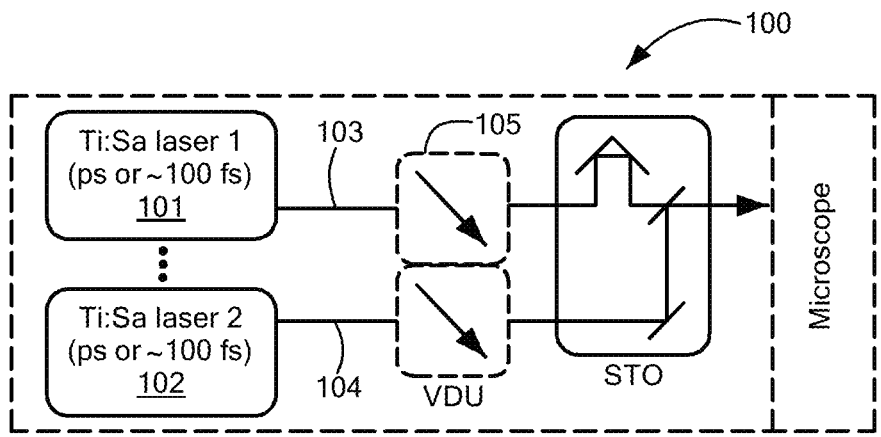
FIG. 1A shows a prior art dual-laser apparatus where synchronized pump-Stokes pulses of a first solid-state laser are combined, using spatial-temporal overlapping (STO), with a tunable differential optical frequency of a second solid-state laser.

Definitions: The term "extracellular vesicle" (EV) is used in an inclusive sense, encompassing any extracellular structure in a biological organism that is bounded by a lipid bilayer. The term includes exosomes and microvesicles, in particular but without limitation.

An "untagged" molecule is a molecule to which no label or probe has been attached.

A "wavelength band" of light is a term used herein to refer to electromagnetic energy characterized by a spectrum that is simply-connected in frequency space.

The terms "object," "sample," and "specimen" shall refer, interchangeably, to a tangible, non-transitory physical object amenable to being rendered as an image.

The term "biological sample" shall encompass any material associated with an organism that is, or once was, alive, including, without limitation, tissue, urine, liquid surgical waste, blood, etc.

The adjective "arbitrary" or adverb "arbitrarily," as used herein, signify allowing for exercise of the discretion of an operator of a system in accordance with the invention to specify a parameter or operating condition.

The term "in-situ" shall refer to study of a biological specimen within its biological context.

The term "concurrent" imaging refers to temporal multiplexing of different imaging contrasts in one pixel dwell time, as applied in various spectroscopic imaging techniques.

"Simultaneous" multimodal imaging is here defined as the spectral multiplexing of different detection channels in one pixel dwell time. It is to be understood that at least one excitation pulse must fall within a single pixel dwell time.

A "supercontinuum distribution" of light is sometimes taken as a spectrum of light energy that does not fall by more than 30 dB over a broad range of wavelength, however the term is used here in a general sense and without specific limitation.

A supercontinuum distribution of light shall be referred to as "coherent" if it may be compressed to form an ultrashort pulse. The coherence of a supercontinuum pulse is rigorously defined in Dudley et al., "*Coherence properties of supercontinuum spectra generated in photonic crystal and tapered optical fibers,*" Opt. Lett., vol. 27, pp. 1180-1182 (2002), which is incorporated herein by reference.

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereon. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

The term "extracellular vesicle" shall be used herein in a general sense, referring to any generally spherical structure of biological molecules characterized by a diameter less than 1 µm. A "biological molecule" is a molecule that is produced by a cell or a living organism, including, typically, carbohydrates, proteins, nucleic acids and lipids.

The term "active beam" shall be defined as a beam of light emitted from a cavity that encloses a medium exhibiting gain over the spectrum of the beam.

The term "passive beam" shall be defined as a beam of light, the spectral characteristics of which are defined by a medium that does not exhibit gain within the spectrum of the beam.

Physical parameters (such as spectrum, transverse mode shape, and polarization, for example) of a passive beam are typically less sensitive to ambient conditions than are the same parameters of an active beam.

The term "laser-microscope alignment decoupling" is rigorously defined herein as the implementation of an optical configuration wherein the illumination of a sample at, or near, the focus of a microscope objective is entirely insensitive to alignment of a laser employed as a source of illumination or excitation.

Visualizing unlabeled extracellular vesicles (EV) in situ, in an unperturbed tumor microenvironment, for example, is made possible for the first time using methods in accordance with the present invention as now described. Through application of techniques described and claimed herein, a direct link is revealed between EV enrichment and a metabolic switch toward biosynthesis. Thus, these vesicles may serve as the signaling mediators from tumor cells to abundant stromal cells in order to initiate the metabolic switch, which may, in turn, induce various macroscopic events in the tumor microenvironment.

Both the metabolic switch and extracellular vesicle enrichment are microscopic events in the tumor microenvironment, and are independent of the macroscopic heterogeneity of the sample. This aspect, together with their concurrence at the earliest stages of tumor development, may qualify them as more effective targets for cancer diagnosis and therapeutic intervention than the subsequent macroscopic events. Their concurrence in the precancerous regions may have clinical significance during intraoperative procedures, suggesting that the tumor margin may actually lie well beyond the visually delineated structural tumor boundary that is currently defined histologically.

There has been, hitherto, no way to image unlabeled EVs in situ. In particular, in order to image EVs in situ, it was necessary to achieve simultaneous imaging (as defined above) in at least four nonlinear modalities that included SHG, THG, 2PAF and 3PAF, something that could not be achieved, for reasons discussed above, using technologies that existed prior to the present invention. The present inventors found a novel technology allowing excitation of 3PAF with sufficient intensity to bring the 3PAF signal within the same dynamic range as a concurrently excited THG signal, and, at the same time, limit the average optical power incident on the sample. That technology is now described.

While prior to the present invention multiphoton microscopy exhibited diagnostic capabilities approaching that of hematoxylin- and eosin-stained histology ("H&E histology"), embodiments in accordance with the present invention may advantageously visualize biological organization of mesoscopic (micron-scale) constituents, discriminate cell types in connective tissue, quantify cellular metabolism, and recognize well-known cancer indictors such as collective tumor cell invasion, tumor-associated collagen reorganization, angiogenesis, and lymphangiogenesis in situ in freshly excised (thick) unstained tissues.

Aspects of the present invention may be practiced in a variety of embodiments of a multimodality-empowered microscope, some of which are now discussed with reference to FIGS. 1A-1E.

FIG. 1A shows a dual-laser apparatus 100 of synchronized pump-Stokes pulses of a first solid-state laser 101, such as a Ti-sapphire laser, combined, using spatial-temporal overlapping (STO), with a tunable differential optical frequency, and a second solid-state laser 103, with optional variable dispersion units (VDUs) 105. Vogel et al., "*Multimodal imaging to study the morphochemistry of basal cell carcinoma,*" *J. Biophotonics*, vol. 3, pp. 728-36 (2010), incorporated herein by reference, employed such a system. An intrinsic trade-off exists between a simple setup with high CARS/SRS spectral resolution using picosecond pulses and efficient nonlinear imaging by SHG, THG, 2PAF, and 3PAF using fs pulses.

Figure 1B:
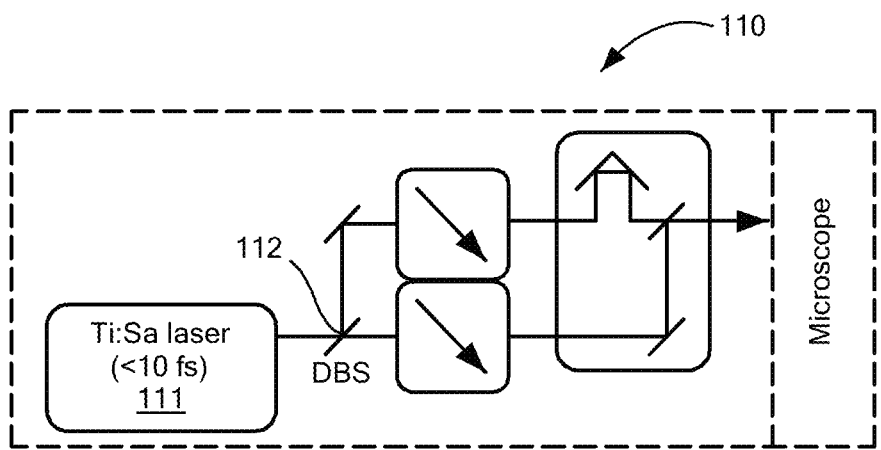
FIG. 1B depicts a prior art apparatus using a single laser to simultaneously access all excitation wavelengths of constituent modalities.
Figure 1C:
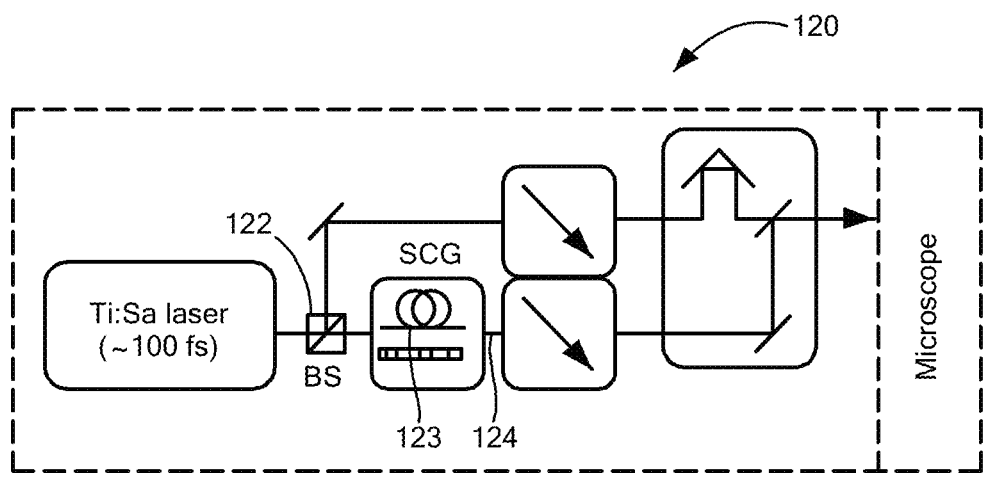
FIG. 1C schematically depicts another single-laser apparatus using a beam splitter (BS) and fiber supercontinuum generation (SCG) to convert an active beam into a passive beam.

FIG. 1B depicts a single-laser apparatus 110, using a single laser 111, which may be a solid-state laser, and one or more dichroic beam splitter(s) (DBS) 112 to simultaneously access all excitation wavelengths of constituent modalities. Such a system is discussed in Pope et al., "*Simultaneous hyperspectral differential-CARS, TPF and SHG microscopy with a single 5 fs Ti:Sa laser,*" *Opt. Exp.*, vol. 21, pp. 7096-106 (2013), which is incorporated herein by reference. FIG. 1C schematically depicts another single-laser apparatus 130, using a beam splitter (BS) and fiber supercontinuum generation (SCG) to convert one "active" beam 122, which is sensitive to ambient conditions, into a "passive" environmentally insensitive beam 124 that is insensitive to conditions of the ambient environment, the spatially properties of which are dictated by a single-mode photonic crystal fiber 123.

Figure 1D:
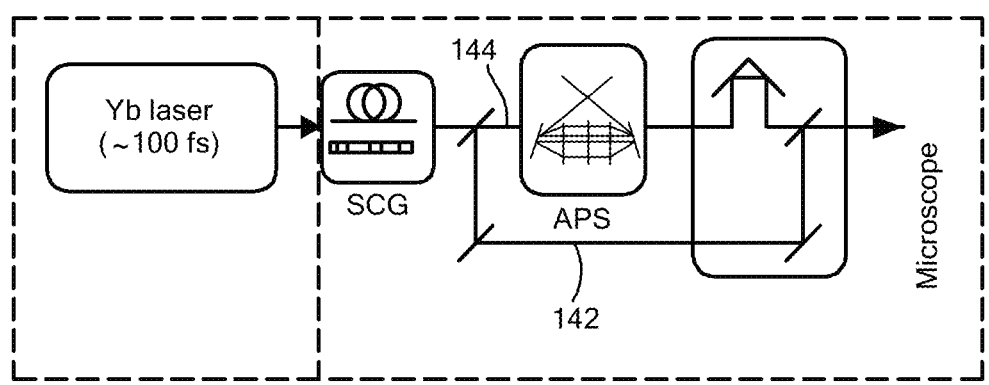
In FIG. 1D, a single-laser apparatus uses supercontinuum generation and arbitrary pulse shaping (to convert two beams into two passive beams.

A single-laser apparatus, designated generally by numeral 140 and now described with reference to FIG. 1D, uses supercontinuum generation (SCG) and arbitrary pulse shaping (APS) to convert two beams 103 and 104 of the conventional dual-laser scheme of FIG. 1A into two passive beams 142 and 144. This scheme incorporates the wavelength tunability of dual-laser apparatus 100 of FIG. 1A, the simultaneous wavelength access of the single-laser apparatus 102 of FIG. 1B, active-to-passive beam conversion of FIG. 1C, and one-laser CARS/SRS spectral focusing from FIGS. 1B and 1C. Because the beam path from the fiber exit end to the sample is determined passively by the fiber, the pulse-conditioning components between laser source and microscope, which are typically treated as an accessory to the laser source, become an accessory to the microscope due to passive beam propagation free of routine optical realignments.

Figure 1E:
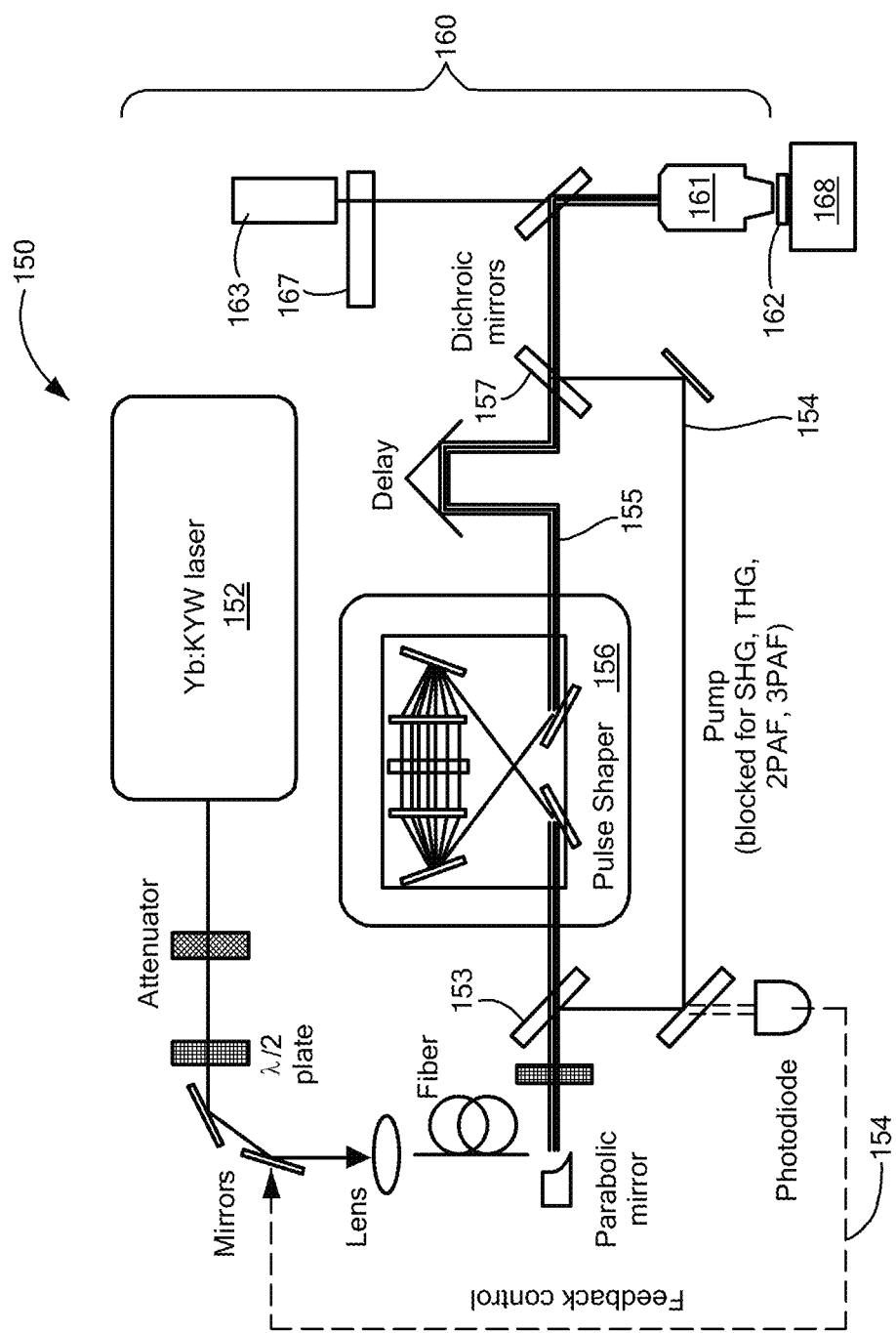
FIGS. 1E and 1F are optical schematics of a multi-modality imaging system in accordance with the present invention.

FIG. 1E is an optical schematic of a multimodality imaging system 150 that is additionally adapted, in accordance with an embodiment of the present invention, to enable laser-microscope alignment decoupling. The beam pointing instability of laser source 152, which is susceptible to day-to-day variations and would demand routine optical realignments to the microscope in the embodiments of FIGS. 1A-1C, is avoided by a feedback control 154 to the laser-fiber coupling mirror to stabilize the fiber output power and guarantee reproducible SCG. The stabilization scheme has been described in Liu et al., "*Suppressing short-term polarization noise and related spectral decoherence in all-normal dispersion fiber supercontinuum generation,*" *J. Lightwave Technol.*, vol. 33, pp. 1814-20 (2015), incorporated herein by reference.

Fiber Supercontinuum Generation

In one embodiment of the present invention, pulses from a Yb:KYW (potassium yttrium tungstate) laser, emitting 1041-nm 220-fs pulses at a repetition rate of 80-MHz, are coupled by an aspheric lens into a 21-cm photonic crystal fiber along the slow-axis of the fiber. This provides for suppression of spectral variation due to changes in ambient conditions. Output (or input) coupling power may be maintained (at 480 or 800 mW, for example) using a feedback control loop. The output is collimated by an off-axis parabolic mirror and sent to a microscope 160 (shown in FIG. 1E). The parabolic mirror was aligned by optimizing the beam shape on a beam profiler at a long distance. Throughout a one-year test period, the supercontinuum spectrum and the corresponding spectral phase have been reproducibly measured in daily operations, not only from one fiber segment but also from other 21-cm fiber segments. This demonstrates the reliable spectral phase stability of this source and ensures reproducible output power and polarization in routine daily operations. Without either the short-term quantum-noise instability or the long-term birefringence-induced instability, the supercontinuum advantageously enables high-quality multiphoton imaging of unstained biological samples.

Use of an Yb-laser-induced supercontinuum is preferred over an Er-laser-induced supercontinuum, but all sources of laser excitation are included within the scope of the present invention. The Yb-laser-induced supercontinuum has three major advantages over the Er-laser-induced supercontinuum: (1) the spectral power is one order of magnitude larger; (2) a longitudinally uniform nonlinear fiber, rather than a specifically fabricated fiber link, is used for supercontinuum generation; and (3) soliton-free supercontinuum generation guarantees high spectral coherence and low optical noise.

Multimodality-Empowered CARS Microscope

Figure 3:
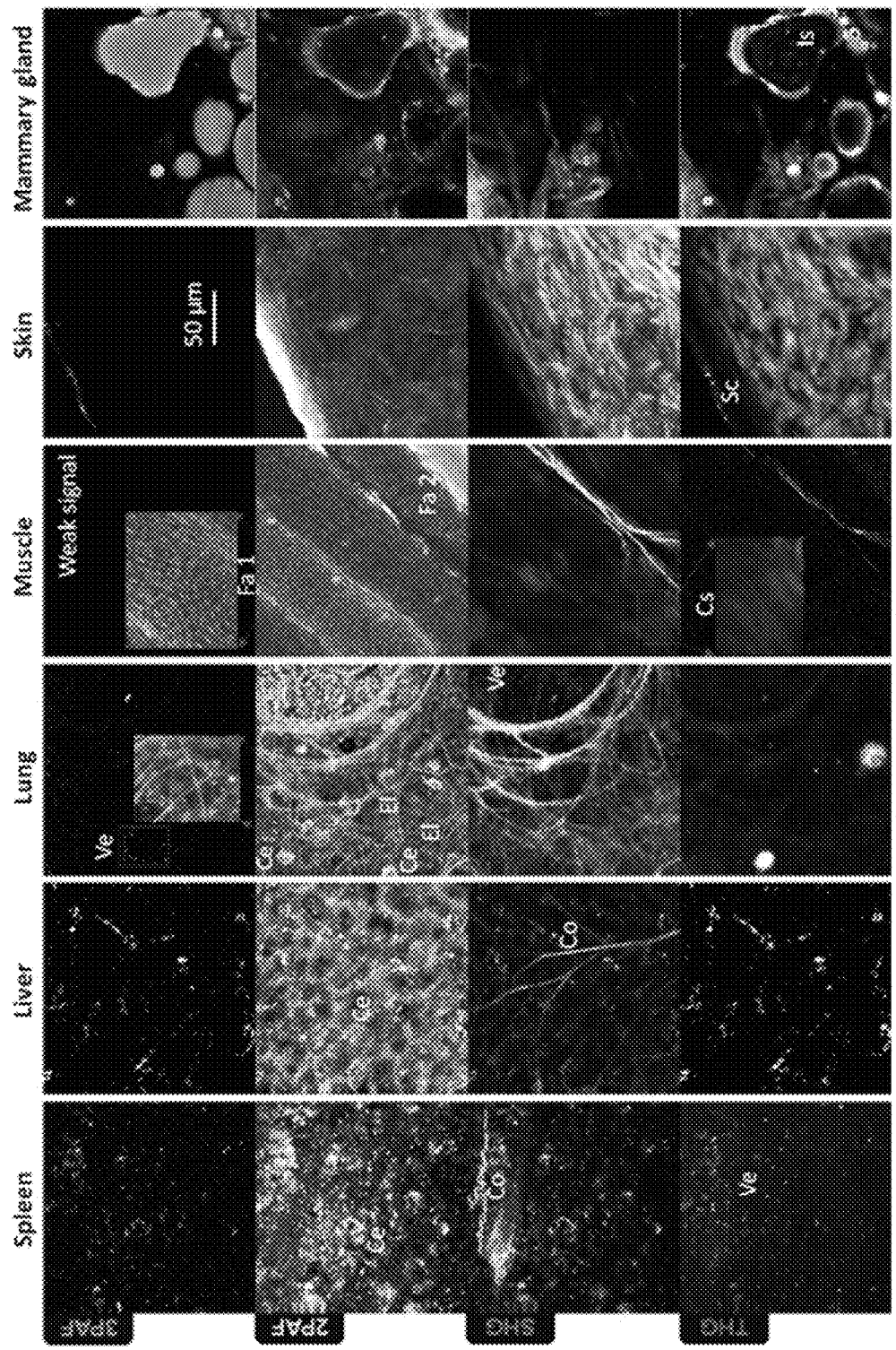
FIG. 3 shows co-localized single-modality multiphoton images and hyperspectral image-integrated CARS spectra of rat organs demonstrating information maximization at each imaging pixel, applying methods in accordance with embodiments of the present invention.
Figure 3:
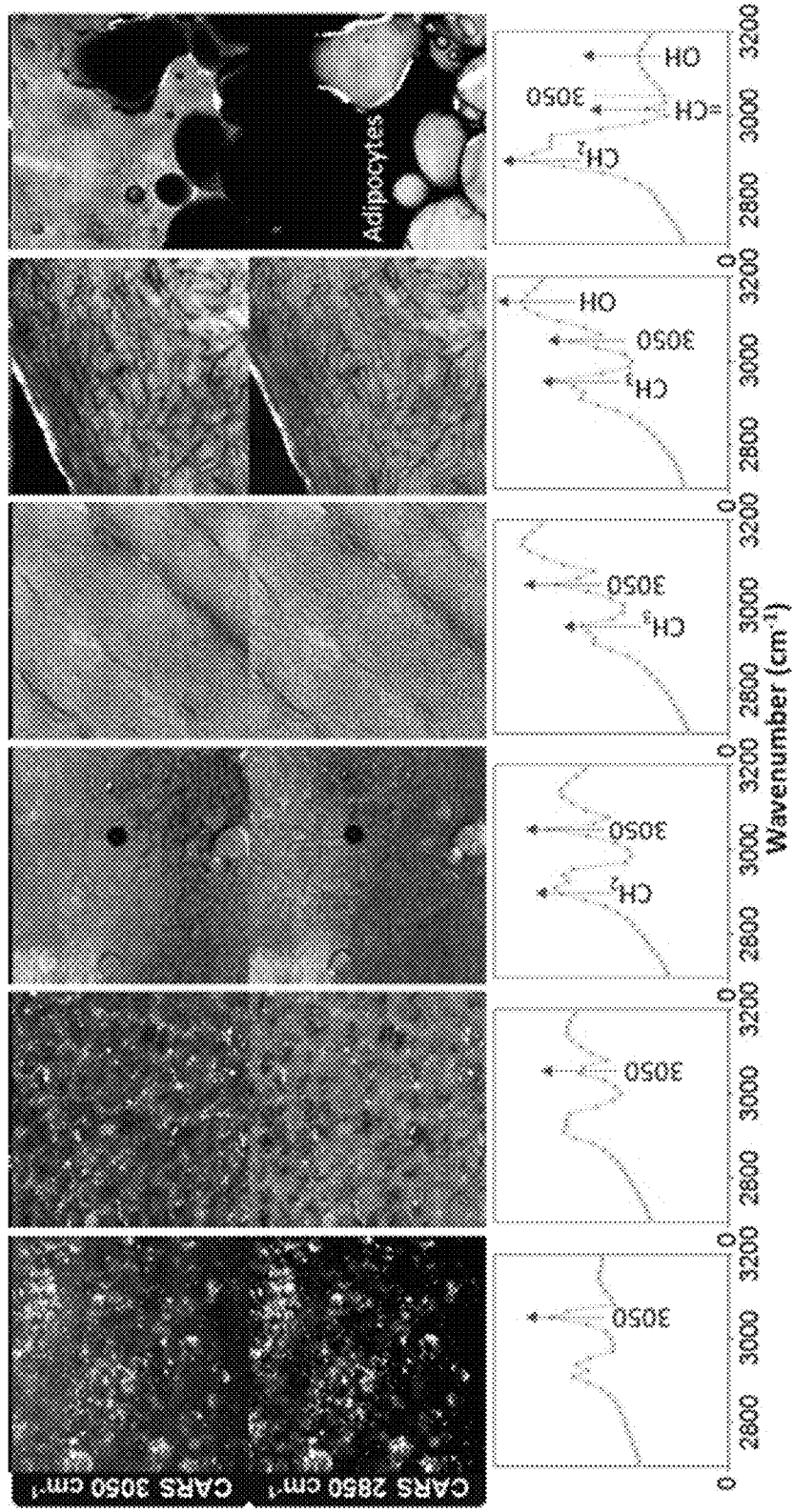

Referring further to FIG. 1E, a dichroic mirror 153 is used to separate the supercontinuum into a CARS pump beam (780-880 nm) 154 and the CARS Stokes beam (900-1320 nm) 155. The Stokes beam 155 is sent into a commercial pulse shaper 156 (available from Biophotonics Solutions of East Lansing, Mich.) for not only CARS imaging, but also 2PAF, SHG, 3APF, and THG imaging. The two beams are then recombined by another dichroic mirror 157, steered, in a single stream of pulses, into a microscope 160 (such as an Olympus Model BX61WI), and focused by an objective 161 (preferably a super-apochromat) on a sample (otherwise referred to herein as a "specimen") 162. A super-apochromat microscope objective enables diffraction-limited imaging independent of excitation wavelengths. Because many common micron-sized biological vesicles show up in all imaging modalities of rat spleen and liver specimens, co-localized multimodal imaging at the same imaging plane can be ensured, as shown in FIG. 3. All the multiphoton signals were collected in the backward (epi-) direction by the same objective 161, spectrally filtered, detected by a common detector 163 (such as a photomultiplier tube) and rigorously calibrated, allowing ex vivo diagnosis of thick tissues, as shown in FIG. 4.

Figure 4:
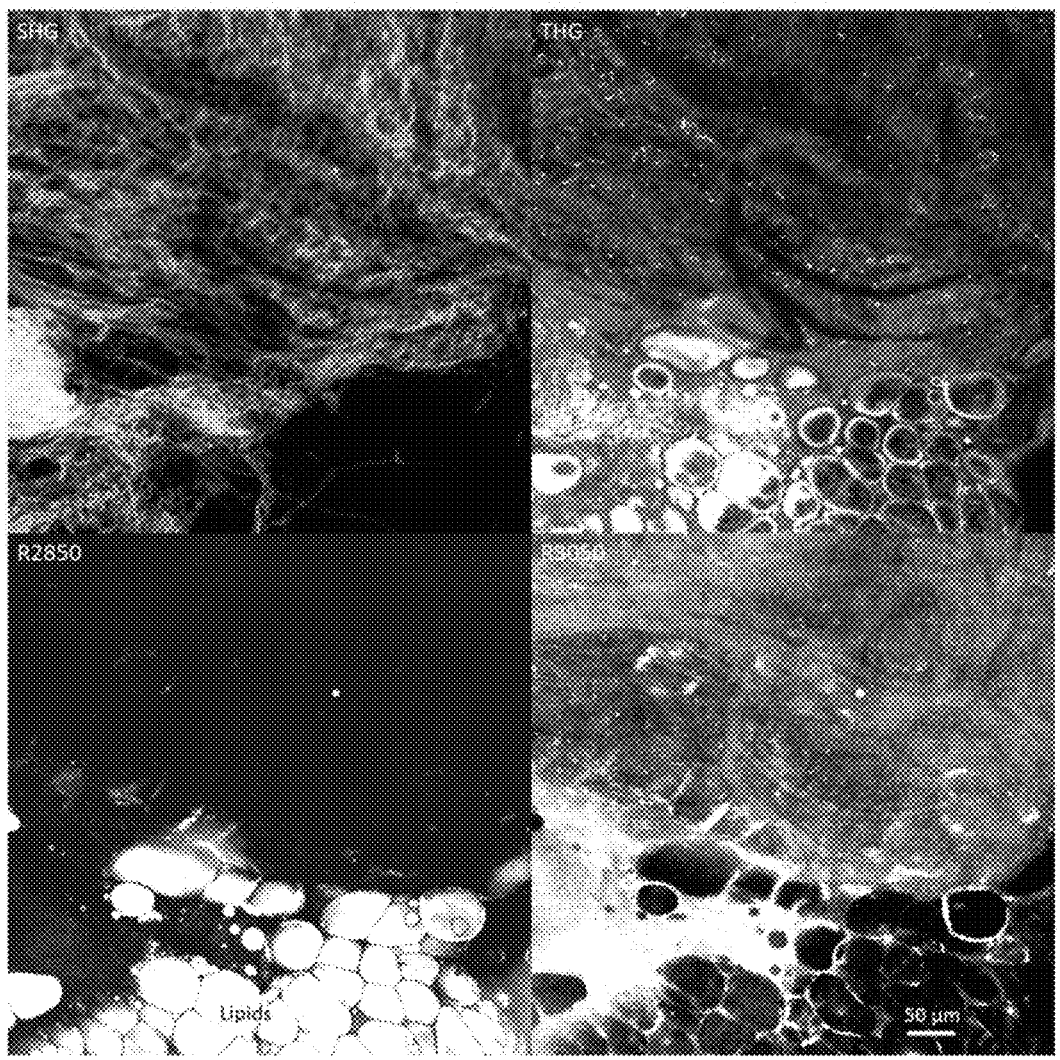
FIG. 4 shows large-area co-localized single-modality multiphoton images from one single section of a tumor margin specimen, applying methods in accordance with embodiments of the present invention.

In FIG. 4 large-area co-localized single-modality multiphoton images from one single section of a tumor margin specimen are shown, demonstrating "seeing things in a different light". When the light is set to SHG imaging, collagen network shows up on the computer screen in one minute (typical time to collect the large-area image for all modalities) and exhibits mysterious voids that cannot be understood within SHG imaging itself (upper left image). When the light is instantly (<1 s) switched to THG imaging, optical heterogeneity of the section replaces the SHG image on the computer screen in one minute, exhibiting the voids more clearly to suggest the presence of blood vessels (upper right image). Because blood vessels are known to generate strong R2850 signal, the light is then switched to R2850 imaging for confirmation (lower left image). However, strong R2850 signal from lipids limits the dynamic range of R2850 imaging, so that no blood vessels can be observed. Finally, the light is switched to R3050 imaging to avoid the lipid signal, and the blood vessels (BV) emerge as a positive contrast in stromal region (lower right image).

Specimen 162 has typical dimensions of 5×5 mm$^2$ area with ~2 mm thickness) is placed on a microscope slide (not shown) and sealed under a coverslip (not shown), while the imaging focal plane is placed ~10 μm below the sample surface. A relatively long pixel dwell time of 200 μs is used for all modalities, which is largely limited by the raster scanning speed (>100 μs pixel dwell time) of a mechanical stage (not shown) to collect images. Typical regular images (380×380 pixels with 0.5 μm pixel size) and large-area images (1100×1100 pixels with 0.5 μm pixel size), require 40 s and 5 min to collect each image.

In the examples discussed below, all SHG, THG, CARS, and 2PAF images are plotted with the same dynamic range using the default setting of ImageJ (National Institutes of Health) from unprocessed raw data. For some 3PAF images that have low signals but recognizable morphological features, the dynamic range (brightness/contrast) to better show these features. Thus, preprogrammed settings allow direct comparison of all modalities within the dynamic range, except for 3PAF. Although 3PAF does not generate strong signals in some specimens, it does in other specimens and uniquely reveals a class of biological vesicles.

Simultaneous tetramodal imaging, including SHG, THG, 2PAF and 3PAF, may be achieved in an in-situ biological specimen, requires a high imaging speed of <20 microsecond per pixel, and the capability to image thick specimens, and no system ever suggested has been able to achieve such performance. The key to achieving such performance is excitation at a wavelength of 1110±30 nm, a pulse repetition rate lower than 30 MHz and/or a pulse duration lower than 100 fs (FWHM). No system existing prior to the present invention has provided that performance, and, thus, in-situ imaging of extracellular vesicles has only now been made possible, in accordance with embodiments of the present invention.

It is to be understood that deriving separate measures of the biological sample, whether or not the sample is imaged, falls within the scope of the present invention as claimed.

Pulse Shaping-Enabled "Virtual" Histochemistry

In accordance with aspects of the present invention, for 2PAF, SHG, 3PAF, and THG imaging of endogenous molecules and structures, pulses of selected spectral ranges (preferably 1110±30 nm) are compressed in time to the transform-limit. This is accomplished by multiphoton intrapulse interference phase scan, as described in Lozovoy et al., "*Multiphoton intrapulse interference. IV. Ultrashort laser pulse spectral phase characterization and compensation,*" *Opt. Lett.*, vol. 29, pp. 775-77 (2004), and using the technique of "local compression," described in Liu et al., "*Suppressing short-term polarization noise and related spectral decoherence in all-normal dispersion fiber supercontinuum generation,*" *J. Lightwave Technol.*, vol. 33, pp. 1814-20 (2015). Both of the foregoing references are incorporated herein by reference. The pulse shaper 156 is utilized to spectrally select (and attenuate, if necessary) the spectral bands (amplitude shaping) and to compensate the spectral phases measured at the objective focus (phase shaping), in a manner described in Liu, Y., Tu, H., Benalcazar, W. A., Chaney, E. J. & Boppart, S. A. Multimodal nonlinear imaging by pulse shaping of a fiber supercontinuum from 900 to 1160 nm," *IEEE J. Sel. Top. Quantum Electron.*, vol. 18, 1209-14 (2012), which is incorporated herein by reference.

For CARS, an additional linear chirp of 4500 fs$^2$ after pulse compression may be introduced into the Stokes beam by phase shaping for optimal performance of spectral focusing within the detection vibrational band of 2700-3200 cm$^{-1}$. The spectrally focused vibrational frequency of CARS is controlled by an electric setting of the optical delay between the pump and Stokes pulses.

The spectral resolution of an embodiment of the invention used in examples described herein was calculated to be 14 cm$^{-1}$ based on the measured FWHM (19 cm$^{-1}$) of the 2913 cm$^{-1}$ peak in the CARS spectrum of dimethyl sulfoxide. This finite spectral resolution of CARS is mostly limited by the finite spectral resolution of the pulse shaper (640 pixels to cover the 750-1350 nm bandwidth). Spectral-focusing CARS was then used to collect hyperspectral CARS images from the biological samples, each of which was obtained at one spectral-focusing delay that was varied among the images. CARS spectral intensity at each spectral-focusing delay (vibration frequency) was calculated by averaging the intensity of all pixels in the hyperspectral image corresponding to that vibration frequency. This simple treatment mimics wide-field Raman spectroscopy and was sufficient to distinguish tumor and normal specimens, as evident in FIG. 5.

Figure 5:
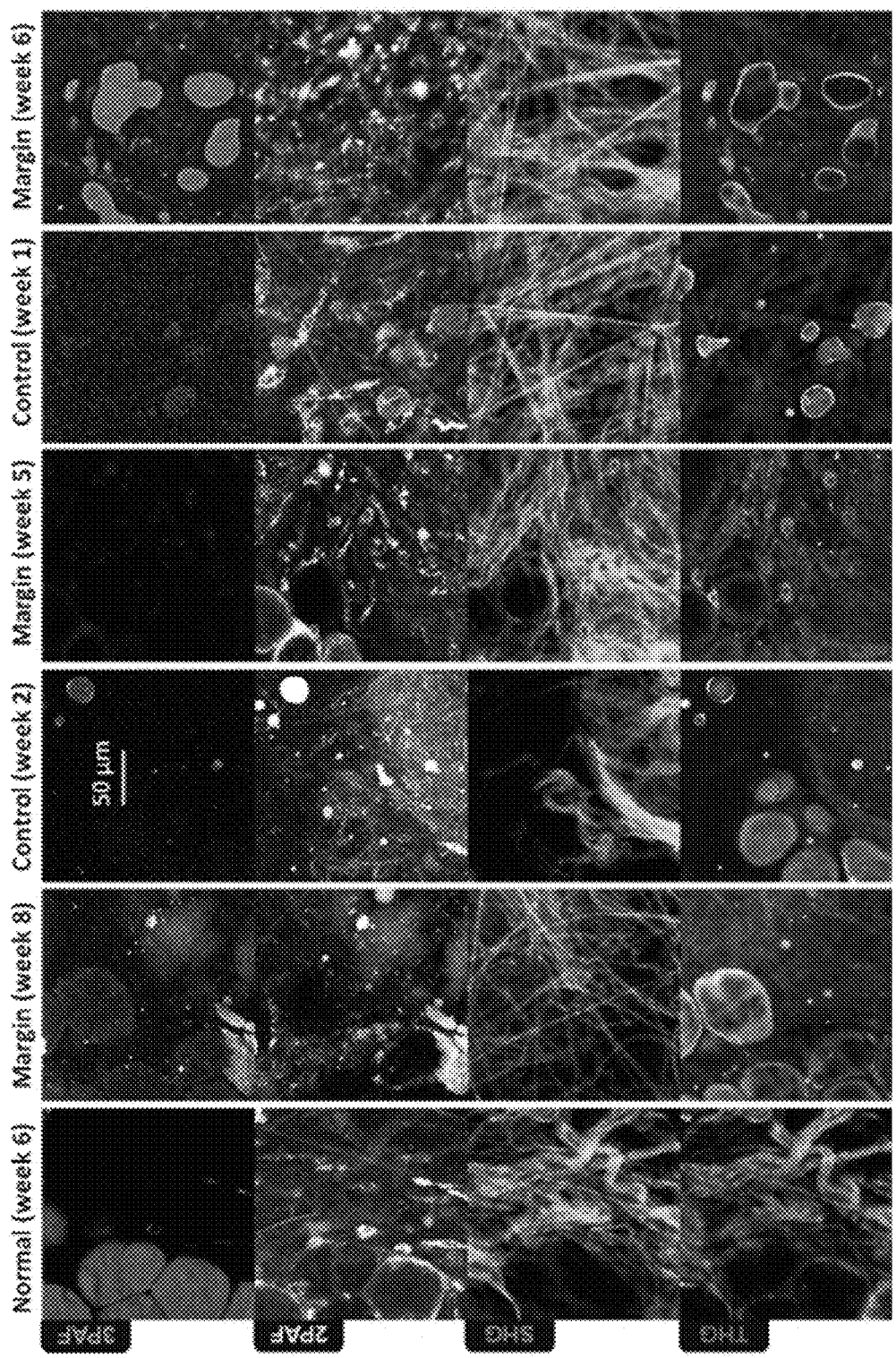
FIG. 5 shows combining co-localized single-modality multiphoton images in mammary adipose-stroma regions with hyperspectral image-integrated CARS spectra to identify a hyperspectral breast cancer biomarker, using methods in accordance with an embodiment of the present invention.
Figure 5:
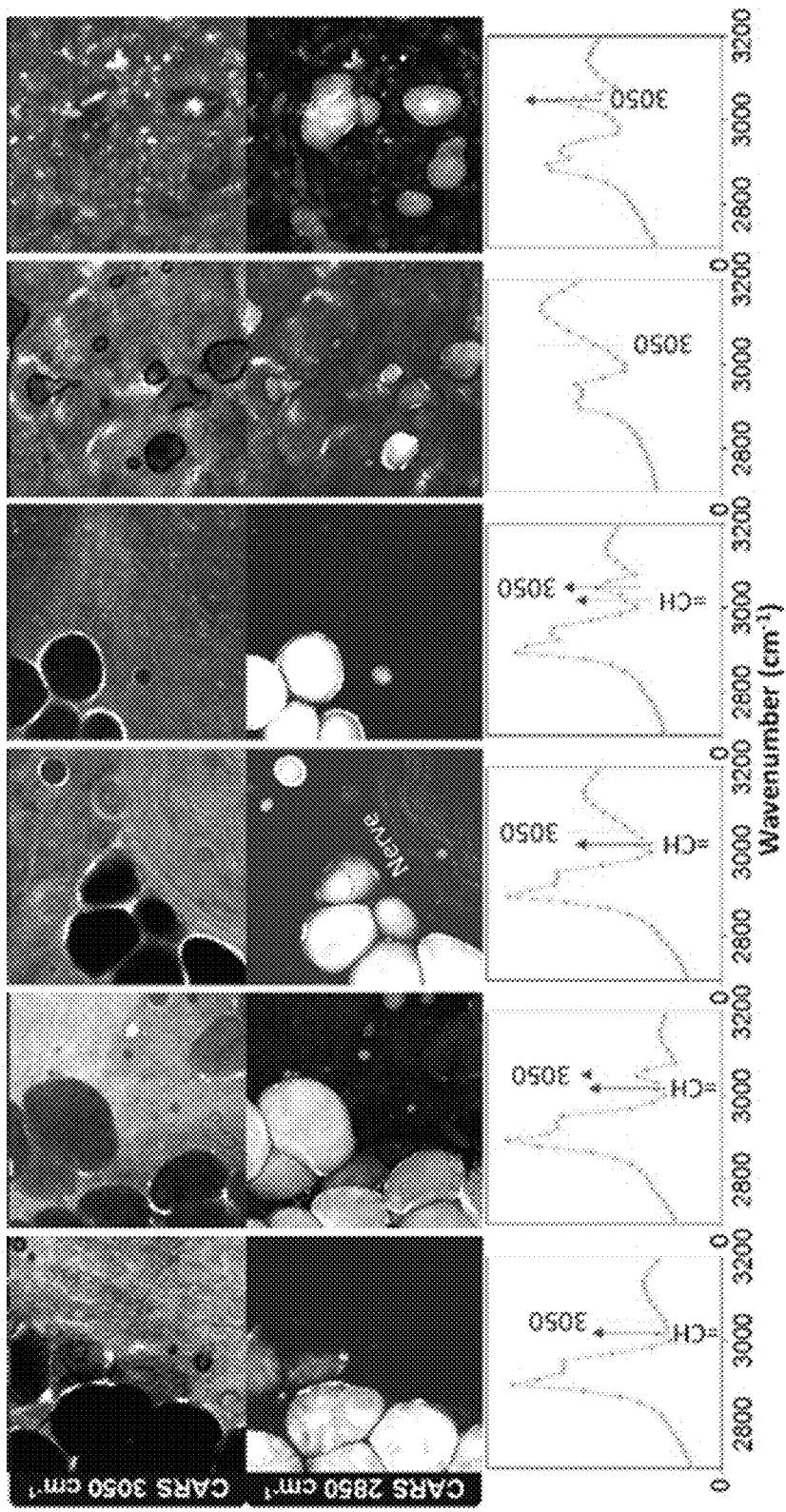

FIG. 5 shows combining co-localized single-modality multiphoton images in mammary adipose-stroma regions with hyperspectral image-integrated CARS spectra to identify a hyperspectral breast cancer biomarker. Normal specimen is from the normal appearing tissue far away (>10 mm) from a palpable week 6 tumor, control specimens are from saline-injected rats, and margin specimens are from tumor margin sites approximately 1 mm away from palpable tumors. The left and right pairs of columns are collected from specimens with and without a clear adipose-stroma boundary, respectively, while the middle pair of columns lies between the two extremes. Although subtle morphological differences may be found in each pair of columns to differentiate tumor and control/normal specimens, the more reliable difference is the emergence of the 3050 cm$^{-1}$ peak in the CARS spectra of the tumor specimens.

Thus, pulse shaping enables optimization of optical signal generation across different modalities. The amplitude and compensation phase masks were then preprogrammed and applied in all imaging sessions. This can then demonstrate that exposing a biological sample to pulse-shaped excitations generates imaging contrast similar to staining the sample with various dyes or fluorescent antibodies. In other words, the endogenous biomolecules in various biological samples can be "artificially" (non-invasively) labeled by pulse-shaped excitations along certain detection spectral-channels, rather than being "physically" labeled by exogenous stains or other fluorescent agents.

Label-Free Nonlinear Optical Imaging with Multiple Contrasts

In accordance with certain embodiments of the present invention, the excitation pulses may be customized for the multiple imaging modalities and amplitude/phase shaped from the supercontinuum and paired with various detection filters 167 to target different endogenous molecules or structures of interest. The incident power of the phase-shaped supercontinuum pulses may be attenuated by amplitude shaping to conservatively safe levels so that no sample damage is observed and the same sample may be repeatedly imaged by different modalities.

Image acquisition may be performed by raster scanning a piezoelectric stage 168 with a pixel dwell time of 200 μs for all modalities. To generate a strong and high-spectral-resolution $\chi^{(3)}_{CARS}$ signal, the spectrally dispersive power of the supercontinuum may be concentrated into a single vibrational frequency by spectral focusing, in which both the pump and Stokes pulses are chirped so that their instantaneous frequency difference remained the same during their interaction time to coherently drive a single molecular vibration, described in Pegoraro et al., "*Optimally chirped multimodal CARS microscopy based on a single Ti: sapphire oscillator,*" *Opt. Expr.*, vol. 17, pp. 2984-96 (2009), which is incorporated herein by reference. Spectroscopic acquisition may be achieved by scanning the delay between two pulses to tune the frequency difference with a spectral resolution of 14 cm$^{-1}$, calculated from the measured FWHM (19 cm$^{-1}$) of the 2913 cm$^{-1}$ peak in the $\chi^{(3)}_{CARS}$ spectrum of dimethyl sulfoxide.

Figure 6:
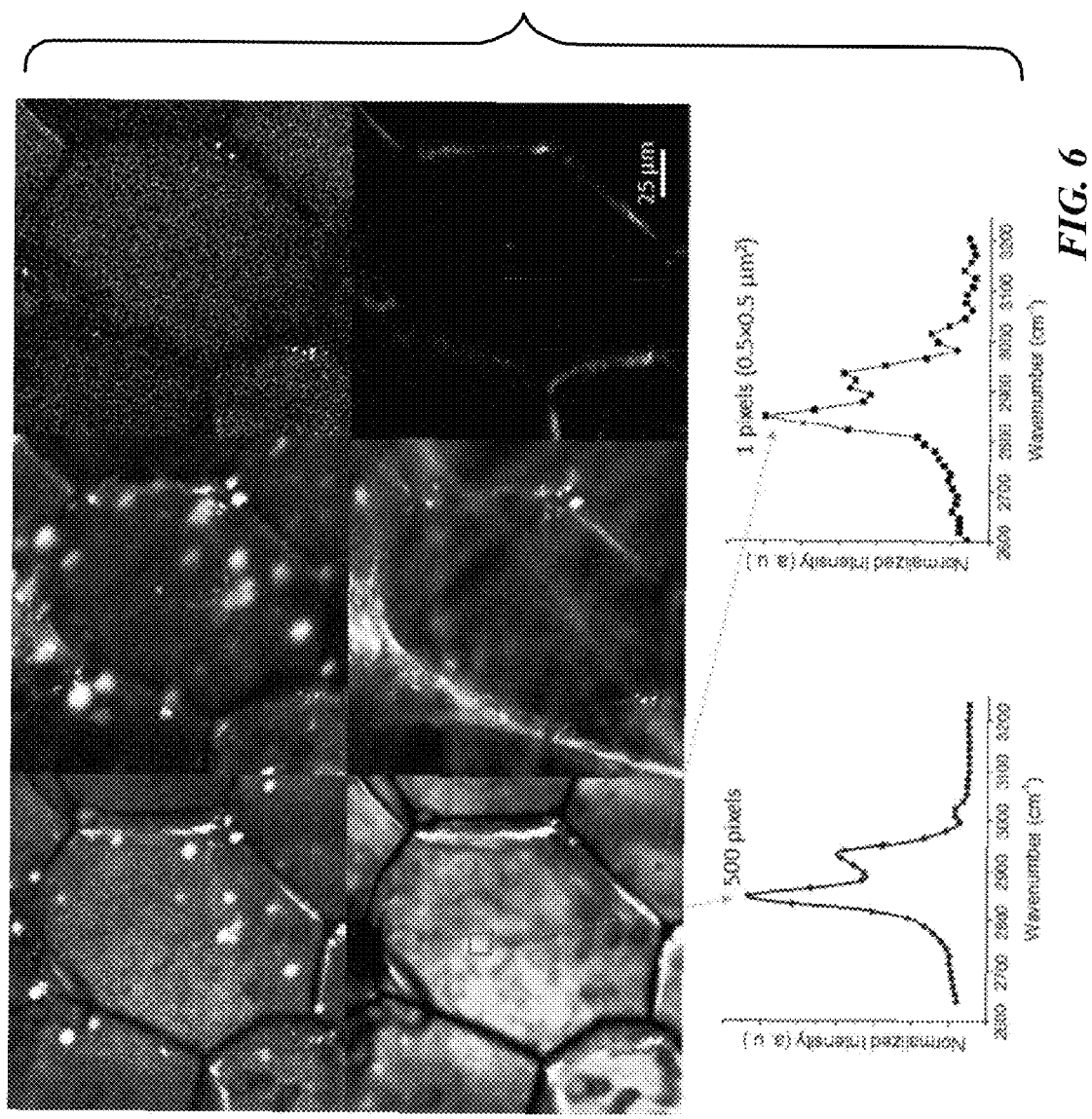
FIG. 6 shows co-registered single-contrast images of an unperturbed normal human mammary specimen. Pseudo-color representations: red-$\chi^{(3)}_{R3050}$ (upper left) or $\chi^{(3)}_{R2850}$ (lower left); yellow—$AF^{(2)}$; green—$\chi^{(2)}_{SHG}$; cyan—$AF^{(3)}$; magenta—$\chi^{(3)}_{THG}$.

Spectral-focusing CARS, as heretofore described, may be used to collect hyperspectral CARS images from biological samples, with each image obtained at one Raman vibration frequency that was varied among the images. In various of the examples discussed below, the $\chi^{(3)}_{CARS}$ spectrum at an arbitrarily selected region of interest was calculated from these images over the corresponding pixels. The $\chi^{(3)}_{CARS}$ spectrum from a single-pixel adipocyte region in a normal human breast tissue approximated that of a larger 500-pixel adipocyte region with sufficient signal-to-noise ratio, as shown in FIG. 6. Similar calculations were employed to obtain the local $\chi^{(3)}_{CARS}$ spectra in other features.

Simultaneous Tetra-Modal Epi-Detected Multiphoton Imaging of Vital Unlabeled Tissue The combination of label-free (intrinsic-contrast) imaging with epi-signal detection is desired for the clinical translation of laser scanning multiphoton microscopy. This feature distinguishes the (pre-)clinical studies on vital (ex vivo, intravital, and in vivo) unlabeled animal/human tissue from the basic studies on cells, embryos, small organisms, plants, fixed tissue, thin tissue sections, and in vitro samples, which often collect larger signals (enable faster imaging speeds) by forward-directed signal detection and/or exogenous (fluorescent) labeling.

In accordance with embodiments of the present invention, endogenous fluorophores or excited by three-photon absorption at a LW band of 1110±30 nm (i.e., the auto-fluorescence contrast of SW-2PAF is generated through LW-3PAF), using the condition of near transform-limited excitation pulses with a short pulse width T (35 fs vs. reference value m of 150 fs, FWHM value throughout this paper), a low pulse repetition rate f (10.2 MHz vs. a reference value $f_0$ of 80 MHz), a moderate average power <I(t)> of 14 mW, and a relatively short pixel dwell time of 4-20 μs (0.5×0.5 μm² pixel size).

Comparison is now provided between the inventive embodiment that has been described and prior suggestions in the art. First, prior studies have demonstrated fast LW-3PAF imaging by low-f long-T excitation (1 MHz, 509 fs, 1040 nm, 5.9 mW, and 1 μs/pixel)[17] and slow LW-3PAF imaging by short-T regular-f excitation (80 MHz, 17 fs, 1140 nm, 12.7 mW, and 200 μs/pixel)[14]. These are described, respectively, in the following two references, both of which are incorporated herein by reference:

Huland et al., "Three-photon excited fluorescence imaging of unstained tissue using a GRIN lens endoscope," Biomed. Opt. Express, vol. 4, pp. 652-58 (2013); and Tu et al., "Stain-Free Histopathology by Programmable Supercontinuum Pulses," Nat. Photonics, vol. 10, pp. 534-40 (August, 2016).

Figure 1F:
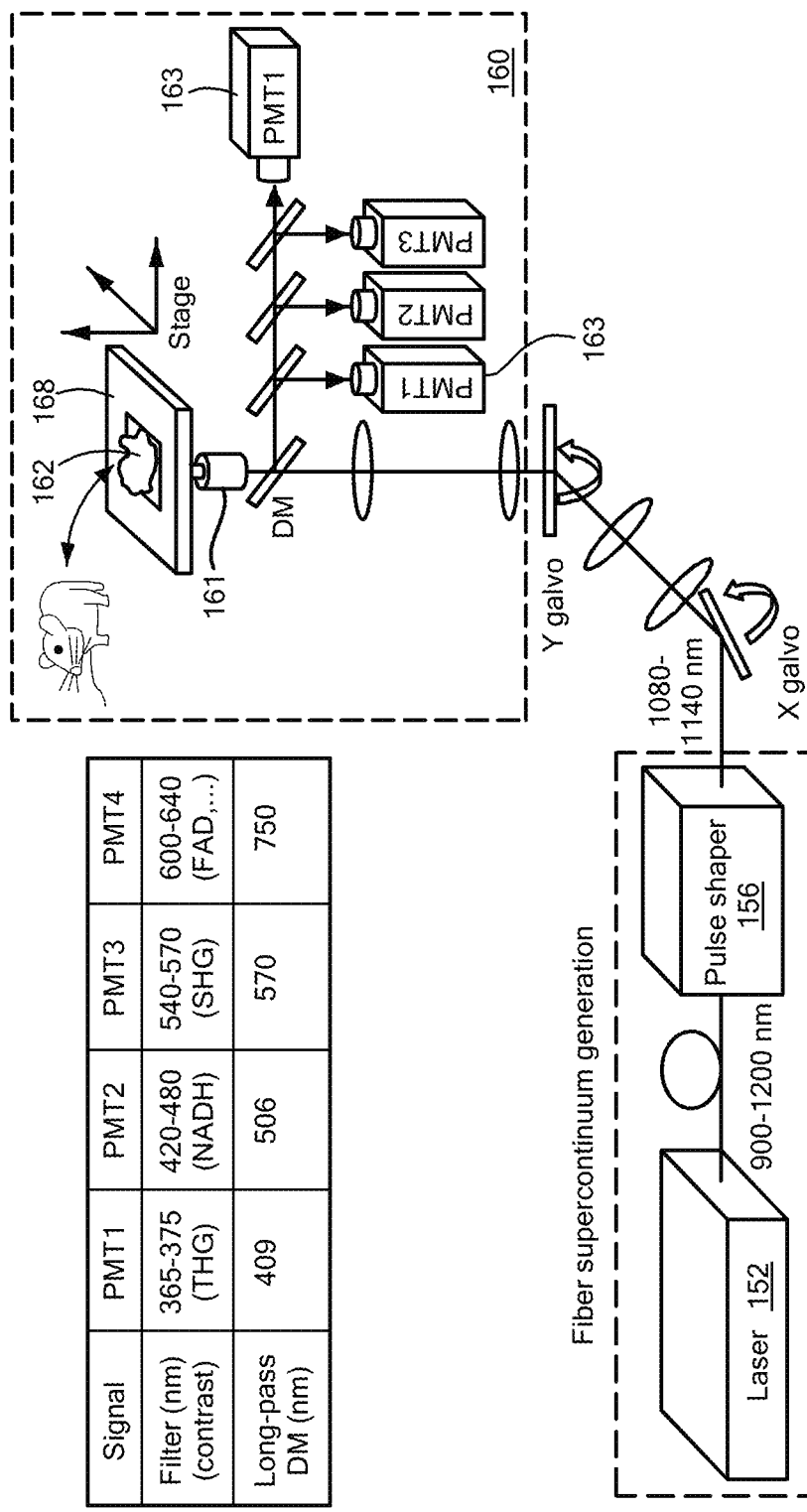

Since nonlinear optical signal (or photodamage) scales with $<I(t)^n>/(f\tau)^{n-1}$ (where n is the order of nonlinear process; n=2 for SHG/2PAF and n=3 for THG/3PAF), it would be expected that a combined low-f and short-T excitation condition, i.e., a large $(f\tau)^{-1}$ (inverse of duty cycle), would enhance the 3PAF signal at a given <I(t)>. Second, the photodamage at a typical LW excitation (1080-1180 nm, 80 MHz, 100-250 fs, 120 mW, 3.3 μs/pixel)' indicates a nonlinear order r between 2 and 3, just like in the case of SW excitation. Thus, by the use of a larger $(f\tau)^{-1}$ coupled with a smaller <I(t)>, the third-order nonlinear imaging by 3PAF or THG gains a favorable signal-to-photodamage ratio (due to 3>r), which would otherwise be unfavorable in the second-order nonlinear imaging by 2PAF or SHG (due to 2<r). Indeed, for a given imaging SNR, a short T of 100 fs has been shown to mitigate the photodamage occurring at 250 fs in THG imaging. Third, the decrease of 2PAF and SHG efficiency from SW to LW excitation may be countered by the increase of $(f\tau)^{-1}$ over $(f_0\tau_0)^{-1}$, so that strong LW-2PAF and LW-SHG signals from animal/human tissue may be collected simultaneously with the 3PAF and THG signals under a safe THG excitation condition, just as in the case of plant specimens, as demonstrated by Chu, 2001. This provides a conceptual basis for simultaneous tetra-modal epi-detected multiphoton imaging, which may be referred to herein as "STEMI," as a matter of convenience, which describes a system denoted generally by numeral 170 in FIG. 1F. STEMI operates at a single excitation band of 1110±30 nm, with four spectrally resolved detection channels of 3PAF, THG, 2PAF, and SHG.

Optimization of the STEMI Condition

In the prior art, optimal excitation wavelength for SHG imaging was placed at around 900 nm for overall good performance in signal strength, tissue penetration depth, and photodamage mitigation. For 2PAF imaging, an excitation wavelength of 750 nm coupled with a blue detection band has been optimized for imaging NADH, while an excitation wavelength of 900 nm coupled with an orange detection band has been optimized for imaging FAD. When THG imaging is considered, the excitation wavelength should lie within 1180-1350 nm to achieve optimal overall performance, although longer wavelengths may be needed to maximize the imaging depth. In STEMI, THG imaging limits the short-end of excitation wavelength to 1080 nm due to UV signal absorption, and 2PAF/3PAF imaging limits the long-end of excitation wavelength to 1170 nm due to low signal strength. The selected wavelength of 1110 nm ensures good imaging depth with less risk of photodamage.

In addition to the excitation wavelength, another important parameter dictating the performance of STEMI is the duty cycle of the mode-locked source laser, i.e., the product of pulse width and pulse repetition rate. A low duty cycle is favorable for generating a large signal, a deep imaging depth and/or a good signal-to-background ratio. This can be either realized by decreasing the pulse width down to sub-15 fs pulses, or by decreasing the pulse repetition rate down to 0.2 MHz. However, slow imaging speed (>1 pulse/pixel) and/or saturation of photon-counting photomultipliers limit the low-end of repetition rate to ~1 MHz, while ambiguous separation of SHG/THG signals from 2PAF/3PAF signals limits the short-end of pulse width to ~15 fs (corresponding to a transform-limited bandwidth of 100 nm @1100 nm). Thus, a combination of moderately short pulse width of 35 fs and moderately low repetition rate of 10.2 MHz in STEMI reflects a reasonable tradeoff.

While mode-locked lasers used for multiphoton imaging in the prior art are dominated by a repetition rate f of ~80 MHz, there are reasons that a lower repetition rate is optimal for label-free multiphoton imaging. First, a decrease off from 80 MHz to 10 MHz brings down the 2PAF (3PAF) saturation power <I(t)> from 30 mW (150 mW) to 4 mW (19 mW), which mitigates cell photodamage and plausible accumulated heating damage. Second, a theoretical study has shown that plasma-mediated nanocavitation dominates the biological photodamage up to f=1 MHz, while free-electron-induced chemical decomposition or accumulated heating dominates the photodamage for f>80 MHz. Thus, the 10 MHz repetition rate may lie in a range where the two different biological photodamage mechanisms occur at higher thresholds. Third, the 10 MHz is more beneficial than 80 MHz in fluorescence lifetime imaging of fluorophores with lifetimes longer than 12.5 ns, so that the accumulating photobleaching can be minimized.

The combination of a relatively long excitation wavelength and a low duty cycle in STEMI allows relatively fast imaging (up to a pixel rate of 250 kHz) at a relatively low average power (14 mW) with minimum risk of photodamage.

Application of apparatus hereto described to achieve novel diagnostic capabilities are now described in detail.

Example I—Carcinogen-Induced Rat Mammary Tumor Model

A well-known preclinical carcinogen-induced rat mammary tumor model was used, and a mammary tumor/tissue specimen (5×5 mm² area with ~2 mm thickness) was excised from a rat six weeks after carcinogen injection. The collection of the multimodal multiphoton images began within minutes after dissection from a site with cleanly delineated adipose and stromal regions, and standard H&E histology was subsequently performed to locate an anatomically similar site for comparison. FIGS. 2A-2C illustrate the mesoscopic organization of biological microstructures revealed in co-localized multiphoton images of two rat mammary specimens and absent from corresponding FFPE-H&E histology images, as now described. Area-integrated CARS spectra over 34 hyperspectral images confirm the presence of a significant R3050 peak as a potential cancer biomarker. FIG. 2A shows that different histochemical components of a tumor are selectively revealed by different single-modality images. Cell cluster 1, in red outline, is identifiable in a 2PAF image, and also in 3PAF, R3050, and R2850 images, reflecting tumor-associated metabolism. The hexagonal radar multiphoton profile (9-pixel average) of a specific type of isolated vesicle, shown in FIG. 2B, approximates that of vesicles aligned in a tubular formation, suggesting that these vesicles are distributed more diffusely before organizing into a tube (indicative of angiogenesis, see text for details). FIG. 2C shows cell cluster 2 (red outline) in a specimen with histologically unidentified cancer from a carcinogen-injected rat is identifiable in a 2PAF image, but not in R3050 and other images, reflecting normal cellular metabolism. Elastin fibers widely observed in connective tissue are shown to be organized into a "basket", which can be linked to lymphangiogenesis (see text for details). Multiphoton image size: 380×380 pixels with 0.5 μm pixel size.

The multiphoton images of R2850 versus R3050 (CARS response at 2850 cm$^{-1}$ versus 3050 cm$^{-1}$), THG vs. SHG, and 3PAF vs. 2PAF demonstrate the largely orthogonal signal contrast of lipids from proteins-water, optical heterogeneity from noncentrosymmetry, and blue auto-fluorescence from yellow FAD auto-fluorescence, respectively. These multiple contrast mechanisms highlight the diverse histochemical and structural components of the specimen, particularly the 3PAF-visible sub-micron-sized biological vesicles that appear spatially arranged in a tubular formation. The same field-of-view also displays some uniquely 2PAF-visible thin (~1 μm diameter) elastin fibers (EF) known to be present in mammary stroma, shown in FIG. 7. In a second specimen from the same animal, elastin fibers are shown to have organized into a "basket" in adipocyte-infiltrated stroma, seen in FIG. 2C.

The only settings varied between the single-modality images in FIG. 2A are to control an electronic amplitude-phase mask of the pulse shaper for tailored excitation to pair with a switchable spectral channel for signal detection (Table 1), and an electronic setting of optical delay that sets the CARS vibrational frequency. Since these settings can be rapidly tuned (<10 ms) or switched under programmable control, different histochemical components can be selectively revealed in different single-modality images. By varying the light with agile pseudo-continuous programming, the contrast of these components against their background may be advantageously rapidly tuned to discover the otherwise obscured biological vesicles and fibers.

*spatial light modulators,*" Rev. Sci. Instrum., vol. 71, 1929-60 (2000), which is incorporated herein by reference. Thus, an operator with no laser and optical alignment training may advantageously selectively display the spatial distribution of a specific endogenous substance on the computer screen, or instantly (and remotely, if necessary) change the imaged substance to a different one by pushing preprogramed buttons to control the excitation/detection, with neither histological stains nor optical realignments.

Example II—Quantitative Breast Cancer Biomarkers

A potential quantitative breast cancer biomarker was demonstrated for the first time in the rat model discussed above. It was discovered that tumors can be objectively discriminated against non-tumor specimens by the emergence of an R3050 spectral peak in the hyperspectral image-integrated CARS spectra, shown in FIGS. 2A-2C and 8. This R3050 signal is not from the carcinogen (N-nitroso-N-methylurea) injected into the rats because spectral focusing of CARS on a saturated water solution of the carcinogen (1.4% by weight) did not yield any signal at R3050. Because regions within mammary specimens can be largely classified into stromal regions (FIG. 7 and adipose regions (FIG. 9) that account for 25% and 75% of the total area from control specimens, respectively, it is more representative to examine comparable tumor and non-tumor specimens that contain both regions.

Figure 9:
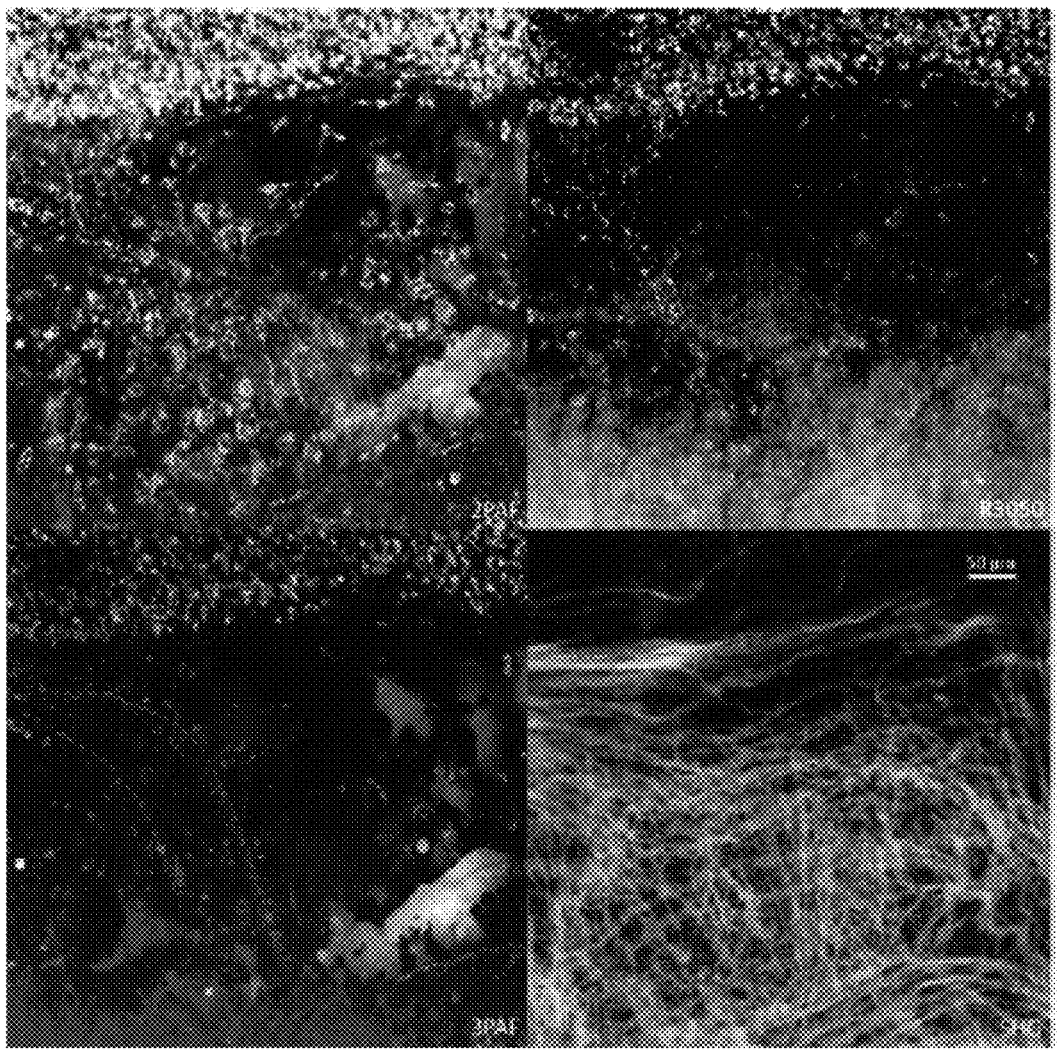
FIG. 9 combines co-localized single-modality multiphoton images in mammary adipose regions with hyperspectral image-integrated CARS spectra to identify hyperspectral breast cancer biomarker, using methods in accordance with an embodiment of the present invention.

FIG. 9 combines co-localized single-modality multiphoton images in mammary adipose regions with hyperspectral image-integrated CARS spectra to identify hyperspectral breast cancer biomarker. Normal specimen is from the normal appearing tissue far away (>10 mm) from a palpable week 5 tumor, control specimens are from the mammary organs of saline-injected rats, and margin specimens are from tumor margin sites approximately 1 mm away from palpable tumors. Despite the morphological differences among adipose regions, including the presence of other cells

TABLE 1

Specifically preprogrammed excitation/detection parameters used in the study of Example I.

| Constituent modality | Excitation band (nm) | Pulse shape | Filter detection band (nm) | Average power under objective (after shaper) | Target substances (reference) |
|---|---|---|---|---|---|
| 2PAF | 910-970 | Transform limited | 542-582 | 4.2 mW (12 mW) | FAD, elastin |
| SHG | 1140-1200 | Transform limited | 571-600 | 3.3 mW (25 mW) | Collagen |
| 3PAF | 1080-1200 | Transform limited | 417-477 | 12.7 mW (42 mW) | Blue fluorophore(s) |
| THG | 1140-1200 | Transform limited | 381-399 | 7.8 mW (25 mW) | Lipid vesicles, other vesicle$^5$, nerve |
| CARS or SRS | Pump: 780-880 Stokes: 1030-1215 | Linearly chirped | 642-705 | Pump: 6.7 mW (22 mW) Stokes: 6.3 mW (58 mW) | Lipid vesicles, nerve, blood cells, protein/water |

A transformation in the capability of nonlinear imaging and potential clinical translation of multiphoton microscopy is enhanced by laser-microscope alignment decoupling, discussed above with reference to FIG. 1E. Laser-microscope alignment decoupling is advantageously practiced by combining deterministic single-mode coherent supercontinuum generation and the specifiable pulse shaping used typically in precision metrology or telecommunication applications, as taught by Weiner, "*Femtosecond pulse shaping using* among adipocytes in the normal specimen, CARS spectra are dominated by the signal from lipids (the main constituent of adipocytes). No reliable difference can be found to differentiate tumor and control/normal specimens.

The R3050 spectral peak readily differentiates tumor and non-tumor specimens, even though their morphological differences are subtle and tumor cells may not be present. By comparing FIG. 7 with the multimodal images and the integrated CARS spectra from the stromal regions (FIG. 5)

and adipose regions (FIG. 6), we can conclude that this peak emerges only from the stromal regions. In the videos consisting of hyperspectral CARS images, the cancer biomarker manifests itself as a "flash" at R3050 in the stromal regions but not in the adipose regions. This potential biomarker is robust against the presence of marked structures that could have complicated qualitative morphological-based interpretation (FIGS. 1, 2, FIG. 5). Because this region-dependent hyperspectral cancer biomarker cannot be appreciated by either imaging or spectroscopy alone, the advantage of hyperspectral CARS imaging for the detection and spatial mapping of this biomarker is self-evident.

In all tumor specimens, shown in FIGS. 2A-2C, 5, 7 and 8, considerable R3050 signal appears co-localized with the 2PAF-visible tumor cells, which was more pronounced than the R2850 signal that reflects de novo lipogenesis, and thus gives these cells a gray appearance in the composite 2PAF-R3050 images (FIGS. 2A-2C, 8).

Figure 7:
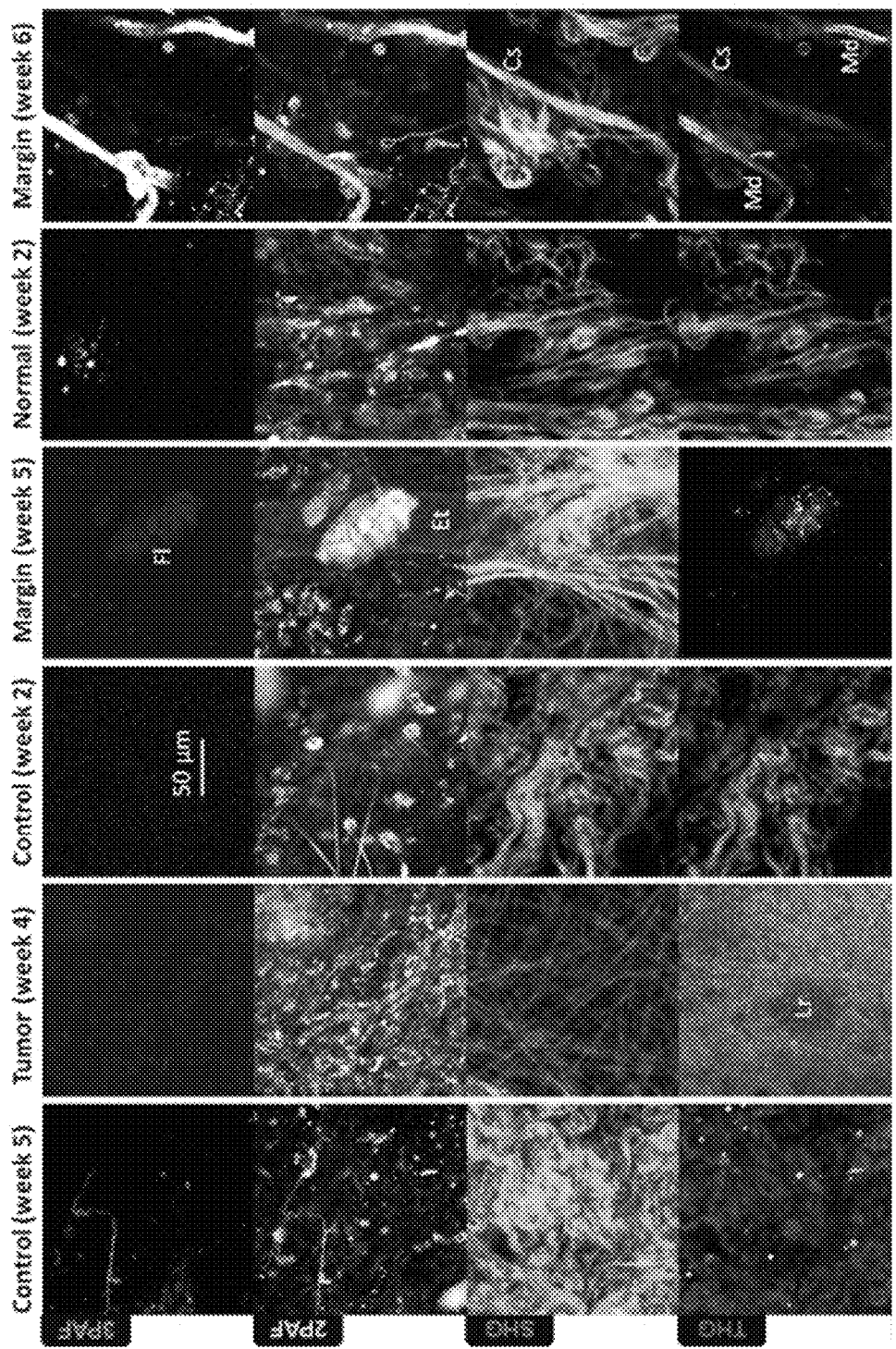
FIG. 7 combines co-localized single-modality multiphoton images in mammary stromal regions with hyperspectral image-integrated CARS spectra to identify hyperspectral breast cancer biomarker, applying methods in accordance with an embodiment of the present invention.
Figure 7:
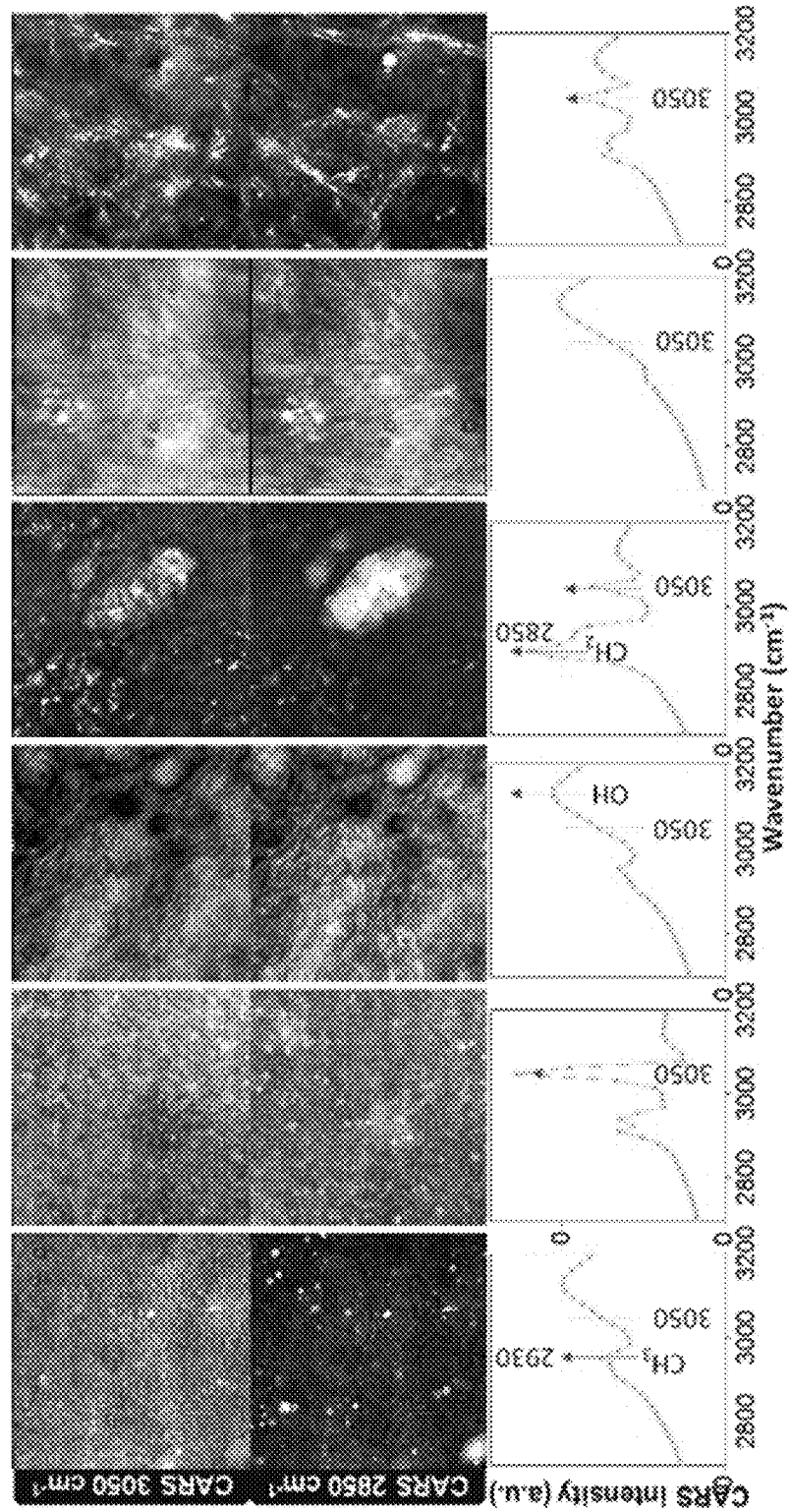

FIG. 7 combines co-localized single-modality multiphoton images in mammary stromal regions with hyperspectral image-integrated CARS spectra to identify hyperspectral breast cancer biomarker, applying methods in accordance with an embodiment of the present invention. Abbreviation: Cs—collagen strand; Et—elastin tube; Fl—fluorescent lipid; Lr—lipid residue; Md—mammary duct. Normal specimen is from the normal appearing tissue of a carcinogen-injected rat with no palpable tumor, control specimens are from the mammary organs of saline-injected rats, and margin specimens are from tumor margin sites approximately 1 mm away from palpable tumors. Although subtle morphological differences may differentiate tumor and control/normal specimens, the more reliable difference is the emergence of the 3050 $cm^{-1}$ peak in the CARS spectra of the tumor specimens.

Figure 8:
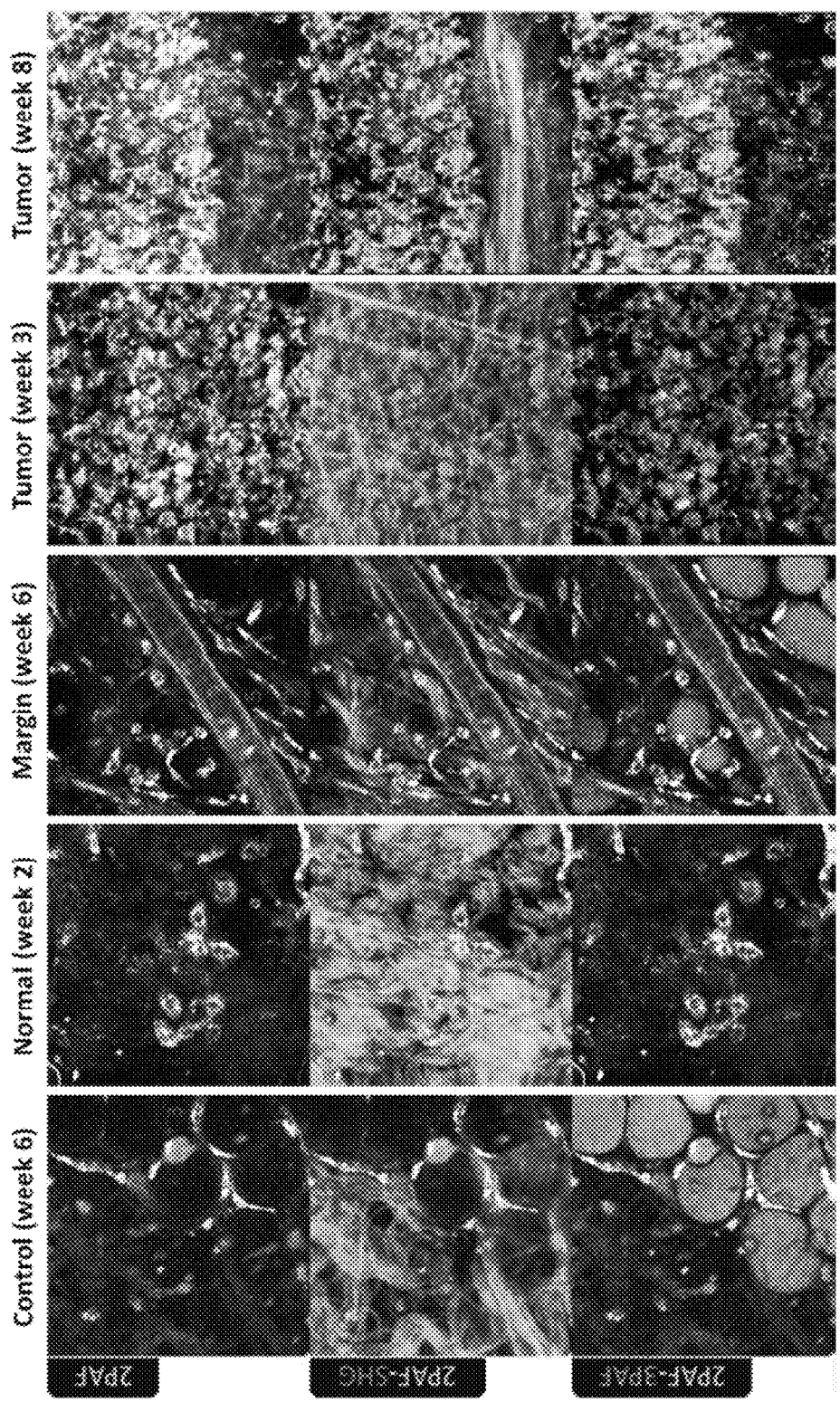
FIG. 8 shows optical signatures in co-localized multiphoton images of five mammary specimens, applying methods in accordance with an embodiment of the present invention.
Figure 8:
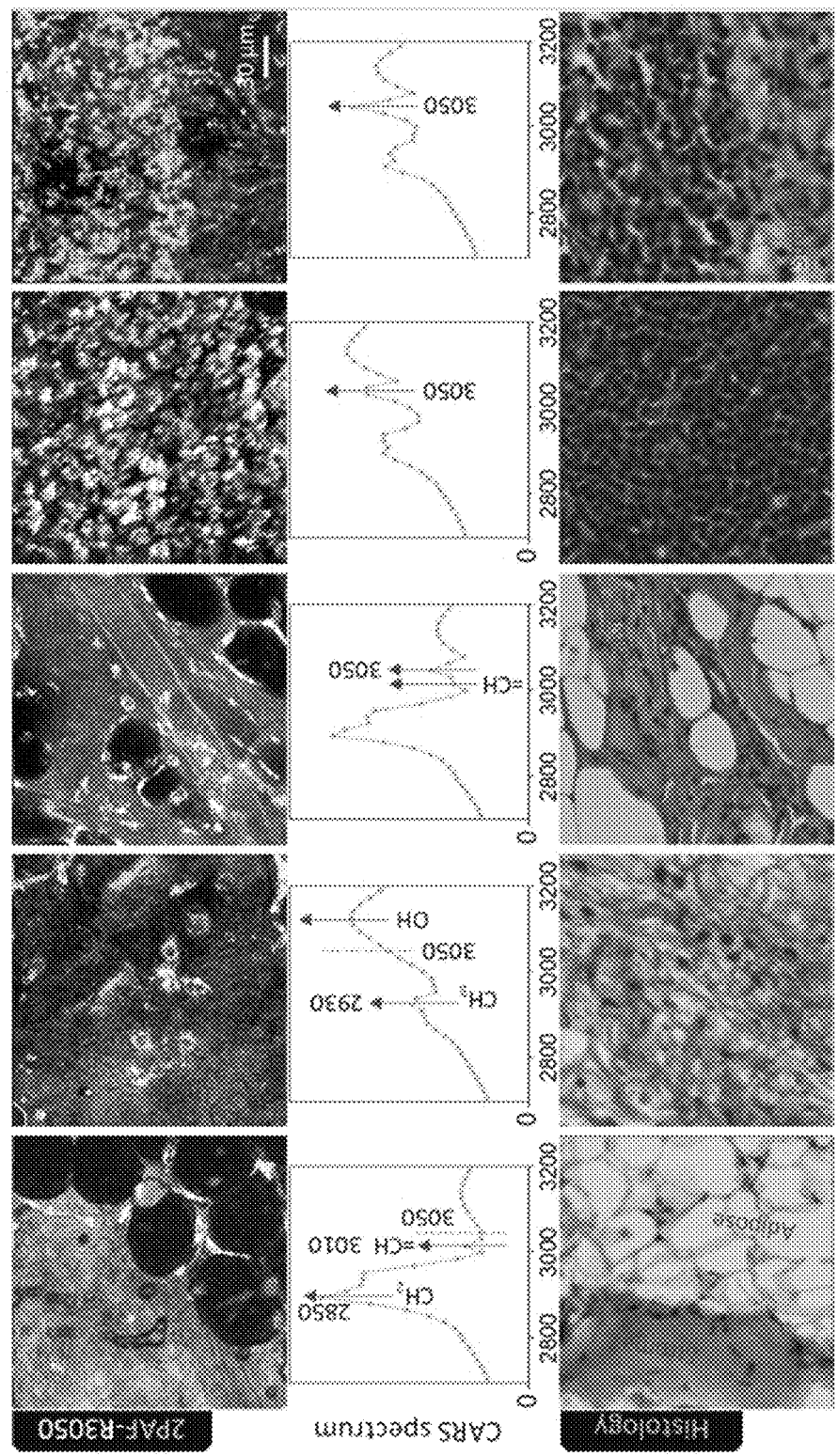

FIG. 8 shows optical signatures in co-localized multiphoton images of five mammary specimens that are absent from corresponding FFPE-H&E histology images. Area-integrated CARS spectra over 30 hyperspectral images reveal common molecular vibrations of $CH_2$ (2850 $cm^{-1}$), $CH_3$ (2930 $cm^{-1}$), =CH (3015 $cm^{-1}$), and OH stretches (3000-3200 $cm^{-1}$), and exhibit a cancer biomarker at R3050, whereas cross-modality visibilities of 2PAF-enhanced cells (encircled in red and labeled #3-7) represent distinct cellular metabolic states. (Bottom row): histology delineates characteristic adipose and stromal regions of control mammary tissue, and reveals cell nuclei located in interstitial spaces among lipid vacuoles of adipocytes with no correspondence between cell nuclei and lipids. In multiphoton images, however, 2PAF-visible cell bodies in the background of 3PAF-visible lipids point to the unique relationship between cell bodies and lipids (red arrows) that form complete adipocytes. (Bottom row, second left): histology of a stroma-only region from a normal appearing mammary specimen (no palpable tumor) from a carcinogen-injected rat displays only some cell nuclei scattered in a distorted collagen fiber network, whereas multiphoton images show how several cells orient themselves in the voids of the collagen fiber network. (Bottom row, middle): histology identifies fibroblasts (blue arrows) from mast cells (magenta arrows) at a tumor margin approximately 1 mm away from a palpable week 6 tumor. In multiphoton images, however, spindle-shaped collagen-producing fibroblasts are aligned with SHG-visible collagen fibers and can be easily differentiated from mast cells near a lymphatic vessel (LV) with flowing lymph (Supplementary Video 4) and a leaky 2PAF-visible basement membrane containing elastin fibers. (Second right): multiphoton images of the inside of a non-palpable tumor reveals cross-linked collagen network that assists tumor invasion. (Right): multiphoton images at a tumor-stroma boundary exhibit vital signatures of local tumor invasion across TACS-2 collagen. Abbreviations: EF—elastin fibers; N—nerve; LV—lymphatic vessel; TACS—tumor-associated collagen structure. Multiphoton image size: 380× 380 pixels with 0.5 μm pixel size.

Non-tumor cells show little contrast in both the R3050 and R2850 images shown in the same figures. Also, mammary tumors seem to generate the R3050-peak phenotype, which was also widely found in normal spleen, liver, lung, skin, and muscle from control rats. The mammary tumor cells in FIG. 8 resemble the biosynthesis-active normal cells in the spleen and liver which exhibit co-localized cell contrast from 2PAF, R3050, and R2850, as evident in FIG. 3.

FIG. 3 shows co-localized single-modality multiphoton images and hyperspectral image-integrated CARS spectra of rat organs demonstrating information maximization at each imaging pixel, applying methods in accordance with embodiments of the present invention. All specimens are from one control rat 2 weeks after saline injection. Since the different physical mechanisms underline the individual modalities, largely different imaging contrasts are obtained from the same section of a specimen. SHG imaging uniquely reveals some collagen fibers (Co) in the spleen and liver specimens. 2PAF imaging uniquely reveals some fluorescent cells (Ce) and elastin fibers (El) in the lung specimen, and two types of filament assembly (Fa) with characteristic cross striations (Cs) in the muscle specimen (see magnified local regions of 2PAF and SHG images). THG imaging uniquely visualizes the stratum corneum layer (Sc) in the skin specimen, and the internal structure (Is) of an abnormal adipocyte in the mammary organ. 3PAF imaging discriminates some fluorescent vesicles against the more abundant vesicles co-visible by SHG and 2PAF in the upper right corner of the lung specimen. These 3PAF-visible vesicles can be confirmed in a co-localized region of the 2PAF image (see magnified local region), but could have been ignored due to strong background. Because many common micron-sized vesicles show up in all modalities for the spleen and liver specimens, the co-localized imaging at the same sample section can be ensured. Hyperspectral CARS imaging yields the integrated CARS spectrum over the whole image, indicating the unique absence of the 3050 $cm^{-1}$ peak in the mammary tissue in comparison to other organs.

This evidence suggests that the metabolic biomolecules associated with the on-and-off R3050 breast cancer biomarker are produced by the tumor cells with a metabolism switched to mainly biosynthesis (Warburg effect), and become transported away from tumors to tumor margins (FIGS. 2A-2C, right, FIG. 8, middle). These findings suggest that the histologically normal specimens exhibit evidence of this R3050 biomarker and its association with early changes in carcinogenesis. These results suggest that the R3050 cancer biomarker could potentially enable cancer diagnosis at a very early stage (week 1), when no tumor is palpable and gross examination is indeterminate (Table 2). The observation of a similar cancer biomarker in humans would potentially allow for early and quantitative diagnosis from small biopsy specimens that may or may not sample the tumors directly.

Example III—Test of 3050 cm$^{-1}$ Cancer Biomarker in Carcinogen-Injected and Control Rat Mammary Tissue Specimens within a Constant Field-of-View (0.19×0.19 mm$^2$)

TABLE 2

Test of 3050 cm$^{-1}$ cancer biomarker in carcinogen-injected and control rat mammary tissue specimens within a constant field-of-view (0.19 × 0.19 mm$^2$).

| Control group (9 rats) | | | Experiment group (9 rats) | | | | | | | |
|---|---|---|---|---|---|---|---|---|---|---|
| | | | Early weeks (1-4) with no palpable tumors | | | | Later weeks (5-9) with palpable tumors | | | |
| Week | Nature of specimen | Bio-marker | Week | Nature of specimen | Gross examination | Bio-marker | Week | Nature of specimen | Gross examination | Bio-marker |
| 1 | S | − | 1 | S | inconclusive | + | 5 | S | tumor margin | + |
| 1 | A-S | − | 1 | A-S | inconclusive | − | 5 | A-S | tumor margin | + |
| 2 | A-S | − | 1 | S | inconclusive | + | 5 | S | tumor margin | + |
| 2 | A | − | 1 | A-S | normal | − | 5 | A-S | tumor margin | − |
| 2 | S | − | 2 | S | normal | − | 6 | A-S | tumor margin | + |
| 3 | A | − | 2 | S | normal | − | 6 | A-S | tumor margin | + |
| 3 | A | − | 2 | S | normal | − | 6 | A-S | tumor margin | + |
| 3 | S | − | 2 | A-S | normal | − | 6 | S | tumor margin | + |
| 4 | A-S | − | 2 | A-S | normal | − | 6 | A-S | normal | − |
| 4 | A | − | 3 | A-S | inconclusive | + | 7 | A-S | tumor margin | + |
| 5 | S | − | 3 | S | inconclusive | + | 7 | A-S | tumor margin | + |
| 5 | A-S | − | 3 | A | normal | − | 7 | A | tumor margin | − |
| 6 | A-S | − | 3 | A-S | normal | − | 7 | S | normal | − |
| 6 | S | − | 3 | A-S | normal | − | 8 | A-S | tumor margin | + |
| 7 | A | − | 4 | A-S | inconclusive | + | 8 | S | tumor margin | + |
| 7 | S | + | 4 | A-S | inconclusive | + | 8 | A | tumor margin | − |
| 8 | A | − | 4 | S | inconclusive | + | 9 | S | tumor margin | + |
| 9 | A | − | 4 | A-S | inconclusive | + | 9 | A-S | normal | − |

Note: All imaging data from the experiment group are included. Nature of specimen is classified into three categories: (a) adipose (A); (b) stroma (S); and (c) both adipose and stroma (A-S). Gross examination of the experimental group was performed by an experienced biologist (E.J.C.) during the surgery and categorized into 3 groups as (1) normal: white and thin mammary gland; (2) histologically inconclusive: slightly darker mammary gland as compared to normal tissue; (3) tumor: palpable tumor mass 0.5-3 mm in diameter with rice-like granular features. For palpable tumor stages (week 5-10), "normal" specimens are from the normal appearing specimens >10 mm away from the palpable tumors, "tumor margin" specimens are from tumor margin areas 1-5 mm away from the palpable tumors. The same gross examination of the control group assigned "normal" status to all specimens, except for the green-highlighted week-7 specimen that is assigned as "inconclusive" (confirmed by the biomarker) and may reflect the natural tumor development in this particular rat. The categorizations of the cyan-highlighted week-1 specimens by the gross examination are "inconclusive", suggesting the plausible advantage of using the hyperspectral biomarker in early-stage cancer diagnosis when tumor is not palpable and gross examination of the specimens is unreliable. The red-highlighted items would be considered as false negative results by wide-field Raman spectroscopy without imaging, but can be disqualified by the imaging-assisted hyperspectral biomarker because the sampling area should not be located exclusively in the adipose regions Example III—Concurrence of Extracellular Vesicle Enrichment and Metabolic Switch Visualized Label-Free in the Tumor Microenvironment The in vivo role of extracellular vesicles has been relatively elusive without observing them label-free in tissue. By visualizing these vesicles in situ in the unperturbed tumor microenvironment, the present inventors have found a direct link of their enrichment with the metabolic switch toward biosynthesis. Thus, these vesicles may serve as the signaling mediators from the tumor cells to the abundant stromal cells in order to initiate the metabolic switch, which may in turn induce various macroscopic events in the tumor microenvironment. Genetic modification of the stromal cells can occur when they accept the vesicles with RNA, according to J. Skog et al., "*Glioblastoma microvesicles transport*

RNA and proteins that promote tumour growth and provide diagnostic biomarkers," *Nat. Cell Biol.*, vol. 10, pp. 1470-76 (2008), incorporated herein by reference. The observations made possible in accordance with the present invention establish the extracellular vesicle enrichment as a fundamental tumor microenvironment event worth further investigation.

Figure 10:
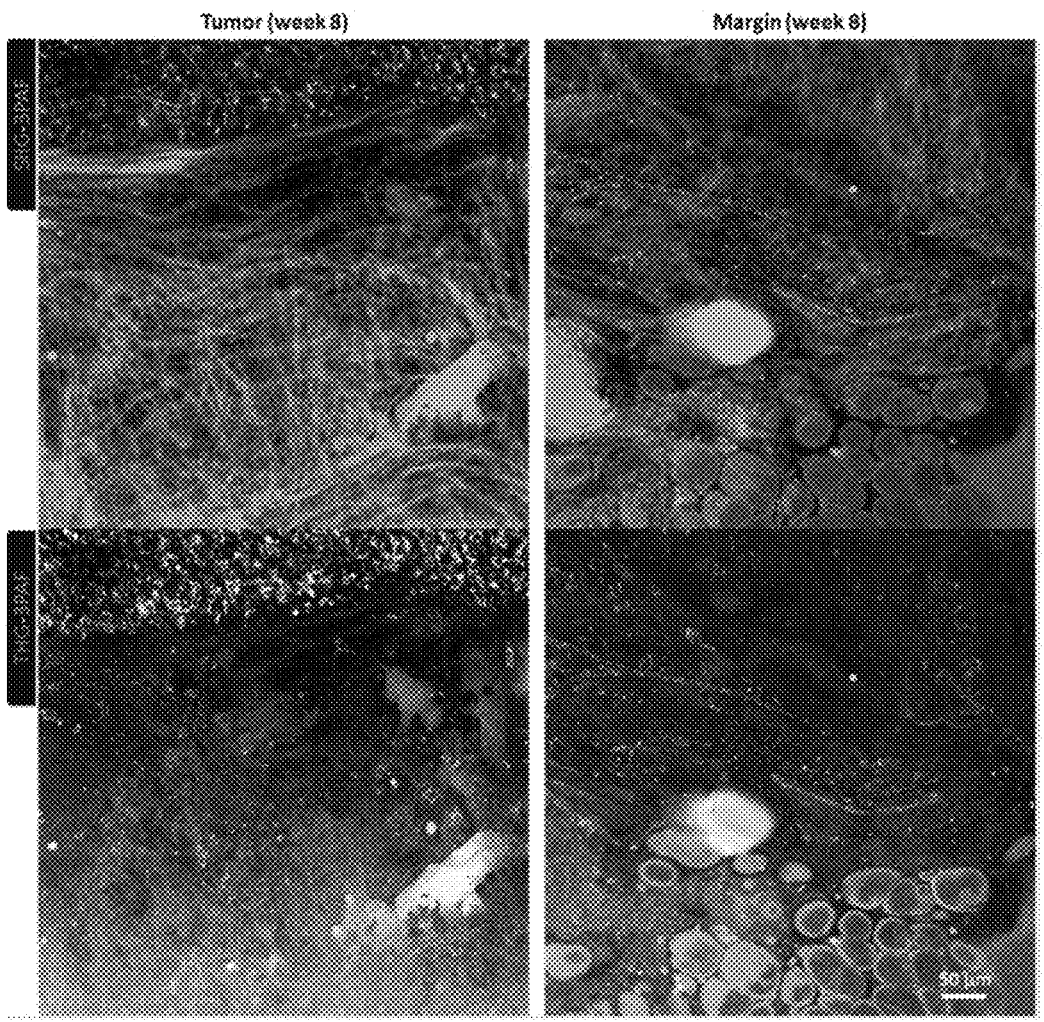
FIG. 10 shows large-area dual-modal multiphoton images from two mammary specimens recognizing biological vesicles in different backgrounds, applying methods in accordance with an embodiment of the present invention.

Referring now to FIG. 10, large-area dual-modal multiphoton images from two mammary specimens recognizing biological vesicles in different backgrounds. The margin specimen was excised 1-5 mm away from the tumor. The infiltration of 3PAF-visible angiogenesis-related (likely tumor-derived) vesicles into stroma along with tumor associated collagen structure-3 can be seen (upper left image). Angiogenesis (An) accommodating collagen reorganization (AACR) can be better resolved after interfering 2PAF background is removed (upper right image). The angiogenesis visualized by the self-organized vesicles may not induce THG-lightened optical heterogeneity (arrows, lower left image), but may do so to generate a negative contrast of optical heterogeneity that matches with the positive contrast of vesicles (arrows, lower right image).

Thus, normal extracellular vesicles may be differentiatied from extracellular vesicles associated with a tumor on the basis of a specified signature of characteristics of images of SHG, THG, 2PAF and 3PAF processes. Differentiation of the normal extracellular vesicles from extracellular vesicles associated with a tumor may employ machine learning. In accordance with one embodiment of the invention, a modified fully convolutional network (FCN) is applied to segment the vesicles (and other biological entities) from the multi-dimensional data based on their morphology, optical signature and surroundings. A variety of features are then used to describe each image site and then selectively combined to predict the disease status. Variables employed include descriptors for each type of biological structures, such as the optical signatures of the segmented vesicles and the density of leukocytes. The variables also include the correlations among different biological entities, such the optical signatures of vesicles in relation to the distance to the nearest tumor cells, and the density of vesicles in relation to the width of the nearest vasculature.

Moreover, it was found that the density of EVs imaged increases proportionally to the number of tumor cells and to the aggressiveness of those cells and tumor, and thus the density of EVs may serve as a measure of tumor aggressiveness. A pilot study shows that a significant portion of vesicles from the tumor micro- and macro-environment have identifiable optical signatures when compared with those from healthy subjects, while, more particularly, combinations of intrinsic optical signals define tumor aggressiveness.

In addition to palpable tumors in a late stage (week 3-9) of tumor development, four additional types of samples were also imaged in a study using the techniques discussed above, as summarized in the following Tables 3 and 4: (a) control mammary specimens from rats without carcinogen injection; (b) normal samples defined as the normal-appearing mammary tissue in early stage (week 1-2) tumor development free of palpable tumors, or 10 mm away from palpable tumors in late stage tumor development; (c) temporally precancerous samples free of palpable tumors but suspicious of early stage cancer development by visual (gross) inspection; and (d) spatially precancerous samples resected 2-5 mm away from palpable tumors suspicious of precancerous development by visual inspection. The typical field-of-view of non-tumor (control or normal) samples consists of approximately 80% adipocyte-dominated regions with 20% stromal regions). The extensive image analysis of tumor and non-tumor samples enables the differentiation of observed macroscopic tumor microenvironment events from certain non-tumor macroscopic events.

Results of a longitudinal animal test of extracellular vesicles and $\chi_{R3050}^{(3)}$ as quantitative breast cancer indicators within a constant field-of-view ($0.19 \times 0.19$ mm$^2$) are shown in Table 3, presented in FIGS. 11A-11C.

Results of a longitudinal animal test of extracellular vesicles and $\chi_{R3050}^{(3)}$ as quantitative breast cancer indicators within a constant field-of-view ($0.57 \times 0.57$ mm$^2$) are shown in Table 3, presented in FIG. 12.

Notes to Tables 3 and 4:

Non-tumor (control or normal) samples, tumor samples, spatially precancerous samples (resected 2-5 mm away from a palpable tumor), temporally precancerous samples (with no palpable tumor), and two samples from an abnormal control rat are highlighted in green, red, violet, orange, and blue in the first column. The tumor samples (on site), spatially precancerous samples, and normal appearing samples (resected 10 mm away from a palpable tumor) linked by one palpable tumor are shaded together in the second column. For the diagnosis by visual inspection: "−" represents white and thin mammary gland; "+" represents palpable tumor mass with orange color and rice-like granular formation; "+1-" represents slightly darker mammary gland suspicious of tumor development. Tumor-associated extracellular vesicles are automatically recognized from $\chi_{THG}^{(3)}$ images by a software procedure that quantifies the prominence of a candidate vesicle and its full-width-at-half-maximum size. For the diagnosis by vesicle count: "+" represents >6 counts; "−" represents <6 counts. Samples with inconsistent diagnosis from visual inspection and two quantitative cancer indicators (vesicle count and presence of R3050 peak) are red-highlighted in the third, fourth, and fifth columns. For the classification of a sampling (imaging) site: "A" represents adipocyte region; "S" represents stromal region; "T" represents tumor region. All images collected in the longitudinal animal study are included for unbiased statistical analysis.

Both the metabolic switch and the extracellular vesicle enrichment are microscopic events in the tumor microenvironment, and are independent of the macroscopic heterogeneity of the sample. This aspect, together with their concurrence at the earliest stages of tumor development, may qualify them as more effective targets for cancer diagnosis and therapeutic intervention than the subsequent macroscopic events. Their concurrence in the precancerous regions may have clinical significance during intraoperative procedures, suggesting that the tumor margin may actually lie well beyond the visually delineated structural tumor boundary that is currently defined histologically.

The simultaneous observation of both microscopic and macroscopic events in these unperturbed tumor microenvironments highlights the advantage of a multicontrast imaging methodology in cancer research and for future assessment of therapeutic strategies. These complex events in carcinogenesis and metastasis could not be easily detected if investigated by only one individual contrast mechanism or imaging modality, or with a lower dimension of combined contrast mechanisms. With presented multiple contrasts, malignant cells and angiogenic vessels can be respectively "labeled" by intrinsic tumor-associated vesicles and tubularly-aligned vesicles to differentiate themselves from normal cells and regular blood vessels. A wide variety of other features in carcinogenesis can also be similarly identified. The use of more invasive exogenous labeling, specific sample treatment, and genetic modification are no longer required to attain this level of imaging so that any associated artifacts are avoided. This investigational approach and visualization methodology is possible in the unperturbed tumor microenvironment to study the complex dynamics and spatially- and temporally-resolved characteristics of tumor cells and tumor-associated extracellular vesicles, with future applications in in vivo pre-clinical animal tumor models as well as in clinical human studies.

Further information concerning subject matter related to the present invention may be found in Tu et al., "*Stain-Free Histopathology by Programmable Supercontinuum Pulses,*" *Nat. Photonics*, vol. 10, pp. 534-40 (August, 2016); and Tu et al., "*Concurrence of extracellular vesicle enrichment and metabolic switch visualized label-free in the tumor microenvironment,*" *Science Advances*, vol. 25, e1600675 (January, 2017).

Both of the foregoing references are incorporated herein by reference.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

We claim:

1. A method for characterizing an untagged molecule within a biological sample in-situ, the method comprising:
   exciting the untagged molecule in the biological sample with at least one wavelength band of light derived from a single stream of optical pulses;
   concurrently detecting light emitted by the untagged molecule within the biological sample by SHG, THG, 2PAF and 3PAF processes; and
   deriving separate measures of the biological sample corresponding to light emitted by the untagged molecule in each of the SHG, THG, 2PAF and 3PAF processes.

2. A method in accordance with claim 1, further comprising imaging at least a portion of the biological sample in at least one of the modalities of SHG, THG, 2PAF and 3PAF.

3. A method in accordance with claim 1, wherein the single stream of optical pulses is derived from a coherent supercontinuum distribution of light energy.

4. A method in accordance with claim 1, further comprising additionally detecting light derived from the single stream of optical pulses by coherent anti-Stokes Raman scattering by the untagged molecules.

5. A method in accordance with claim 4, wherein coherent anti-Stokes Raman scattering is excited by a frequency-chirped pulse.

6. A method in accordance with claim 1, wherein the SHG, THG, 2PAF and 3PAF processes are excited by a single excitation pulse.

7. A method for characterizing extracellular vesicles within a biological sample in-situ, the method comprising:
   a. exciting untagged molecules constituent of the extracellular vesicles in the biological sample with at least one wavelength band of light derived from a single stream of optical pulses;
   b. concurrently detecting light emitted by the untagged molecules of the biological sample by SHG, THG, 2PAF and 3PAF processes; and
   c. deriving separate measures of the biological sample corresponding to light emitted by the untagged molecules in each of the SHG, THG, 2PAF and 3PAF processes.

8. A method in accordance with claim 1, further comprising imaging at least a portion of the biological sample in at least one of the modalities of SHG, THG, 2PAF and 3PAF.

9. A method in accordance with claim 1, wherein the single stream of optical pulses is derived from a coherent supercontinuum distribution of light energy.

10. A method in accordance with claim 1, further comprising additionally detecting light derived from the single stream of optical pulses by coherent anti-Stokes Raman scattering by the untagged molecules.

11. A method in accordance with claim 10, wherein coherent anti-Stokes Raman scattering is excited by a frequency-chirped pulse.

12. A method in accordance with claim 1, wherein the SHG, THG, 2PAF and 3PAF processes are excited by a single excitation pulse.

13. A method in accordance with claim 1, further comprising differentiating normal extracellular vesicles from extracellular vesicles associated with a tumor at least on the basis of a specified signature of characteristics of images of SHG, THG, 2PAF and 3PAF processes.

14. A method in accordance with claim 13, wherein the step of differentiating normal extracellular vesicles from extracellular vesicles associated with a tumor on the basis of a specified signature of characteristics of images of SHG, THG, 2PAF and 3PAF employs machine learning.

15. A method in accordance with claim 13, further comprising characterizing the tumor with respect to a grade associated with aggressiveness of the tumor on the basis of the specified signature of characteristics of images of SHG, THG, 2PAF and 3PAF processes.

16. A method in accordance with claim 15, wherein the step of characterizing the tumor with respect to a grade associated with aggressiveness of the tumor on the basis of the specified signature of characteristics of images of SHG, THG, 2PAF and 3PAF processes employs machine learning.

* * * * *